(12) United States Patent
Yasui

(10) Patent No.: US 10,010,281 B2
(45) Date of Patent: Jul. 3, 2018

(54) PUNCTURE INSTRUMENT, PUNCTURE NEEDLE CARTRIDGE MOUNTED IN PUNCTURE INSTRUMENT, AND METHOD FOR USING PUNCTURE INSTRUMENT AND PUNCTURE NEEDLE CARTRIDGE

(71) Applicant: PHC Holdings Corporation, Minato-ku, Tokyo (JP)

(72) Inventor: Shinichi Yasui, Ehime (JP)

(73) Assignee: PHC Holdings Corporation, Tokyo (JP)

( * ) Notice: Subject to any disclaimer, the term of this patent is extended or adjusted under 35 U.S.C. 154(b) by 342 days.

(21) Appl. No.: 14/646,012

(22) PCT Filed: Nov. 11, 2013

(86) PCT No.: PCT/JP2013/006630
§ 371 (c)(1),
(2) Date: May 19, 2015

(87) PCT Pub. No.: WO2014/083783
PCT Pub. Date: Jun. 5, 2014

(65) Prior Publication Data
US 2015/0305660 A1    Oct. 29, 2015

(30) Foreign Application Priority Data

Nov. 30, 2012  (JP) .................. 2012-261980
Dec. 20, 2012  (JP) .................. 2012-277792
(Continued)

(51) Int. Cl.
*A61B 5/15*    (2006.01)
*A61B 5/151*   (2006.01)

(52) U.S. Cl.
CPC .... *A61B 5/150725* (2013.01); *A61B 5/15113* (2013.01); *A61B 5/15186* (2013.01);
(Continued)

(58) Field of Classification Search
CPC .......... A61B 5/150725; A61B 5/15186; A61B 5/15113; A61B 5/1411; A61B 5/1433; A61B 5/15142; A61B 5/15188
See application file for complete search history.

(56) References Cited

U.S. PATENT DOCUMENTS 5,196,025 A    3/1993  Ranalletta et al.
5,318,583 A    6/1994  Rabenau et al.
(Continued)

FOREIGN PATENT DOCUMENTS

JP    H04-261645 A    9/1992
JP    H06-007329 A    1/1994
(Continued)

OTHER PUBLICATIONS

The Decision of Registration from the corresponding Japanese Patent Application No. 2016-171577 dated Jul. 11, 2017.
(Continued)

*Primary Examiner* — Diane Yabut
(74) *Attorney, Agent, or Firm* — Shinjyu Global IP

(57) ABSTRACT

It is an object of this disclosure to facilitate a series of puncture-related operations in a puncture instrument. In a main case of a puncture instrument, a main rod is provided. An injector rod is mounted to a main rod and includes a lancet holder on one end side. An actuating rod is mounted to the injector rod and has an engagement component on the other end side. A first biasing member biases the injector rod toward the first end side. A manipulation component is provided so as to be slidable in and out through an opening on the other end side of the main case. A locking member is axially supported rotatably by a portion of the main rod between the manipulation component and the injector rod. The locking member includes a first engaged part, a second engaged part and a second biasing member.

14 Claims, 25 Drawing Sheets

(30) Foreign Application Priority Data

| Jul. 30, 2013 | (JP) | 2013-157378 |
|---|---|---|
| Jul. 30, 2013 | (JP) | 2013-157379 |
| Sep. 2, 2013 | (JP) | 2013-181085 |

(52) U.S. Cl.
CPC ........... *A61B 5/1411* (2013.01); *A61B 5/1433* (2013.01); *A61B 5/1513* (2013.01); *A61B 5/150022* (2013.01); *A61B 5/15117* (2013.01); *A61B 5/15142* (2013.01); *A61B 5/15188* (2013.01); *A61B 5/15194* (2013.01); *A61B 5/150412* (2013.01); *A61B 5/150503* (2013.01); *A61B 5/150885* (2013.01)

(56) References Cited

U.S. PATENT DOCUMENTS

| 7,238,192 | B2 | 7/2007 | List et al. |
| 7,879,057 | B2 | 2/2011 | Sakata et al. |
| 8,439,941 | B2 | 5/2013 | Ishikura et al. |
| 8,679,145 | B2 | 3/2014 | Okuyama et al. |
| 8,926,645 | B2 | 1/2015 | Ishikura et al. |
| 2003/0216767 | A1 | 11/2003 | List et al. |
| 2005/0261716 | A1 | 11/2005 | Sakata et al. |
| 2009/0012427 | A1 | 1/2009 | Fukuzawa |
| 2009/0163944 | A1 | 6/2009 | Nagao et al. |
| 2010/0049234 | A1 | 2/2010 | Kitamura et al. |
| 2010/0305601 | A1* | 12/2010 | Karbowniczek ..... A61B 5/1411 606/182 |
| 2011/0015662 | A1 | 1/2011 | Okuyanna et al. |
| 2011/0130781 | A1 | 6/2011 | Sakata et al. |
| 2011/0196409 | A1 | 8/2011 | Nagao et al. |
| 2011/0313439 | A1 | 12/2011 | Ishikura et al. |
| 2012/0095488 | A1 | 4/2012 | Saeki et al. |
| 2013/0238007 | A1 | 9/2013 | Ishikura et al. |

FOREIGN PATENT DOCUMENTS

| JP | 2003-325484 A | 11/2003 |
| JP | 2004-033440 A | 2/2004 |
| JP | 2006-314718 A | 11/2006 |
| JP | 2007-536008 A | 12/2007 |
| JP | 2010-110625 A | 5/2010 |
| JP | 2010-148748 A | 7/2010 |
| JP | 2012-005518 A | 1/2012 |
| JP | 2012-085686 A | 5/2012 |
| WO | 2005/110227 A1 | 11/2005 |
| WO | WO2006/046570 A1 | 5/2006 |
| WO | 2007/129757 A1 | 11/2007 |
| WO | 2007/145205 A1 | 12/2007 |
| WO | 2009/110247 A1 | 9/2009 |

OTHER PUBLICATIONS

International Search Report of corresponding PCT Application No. PCT/JP2013/006630 dated Feb. 4, 2014.

Decision of Patent from the corresponding Japanese Patent Application No. 2014-549786 dated Aug. 9, 2016.

* cited by examiner

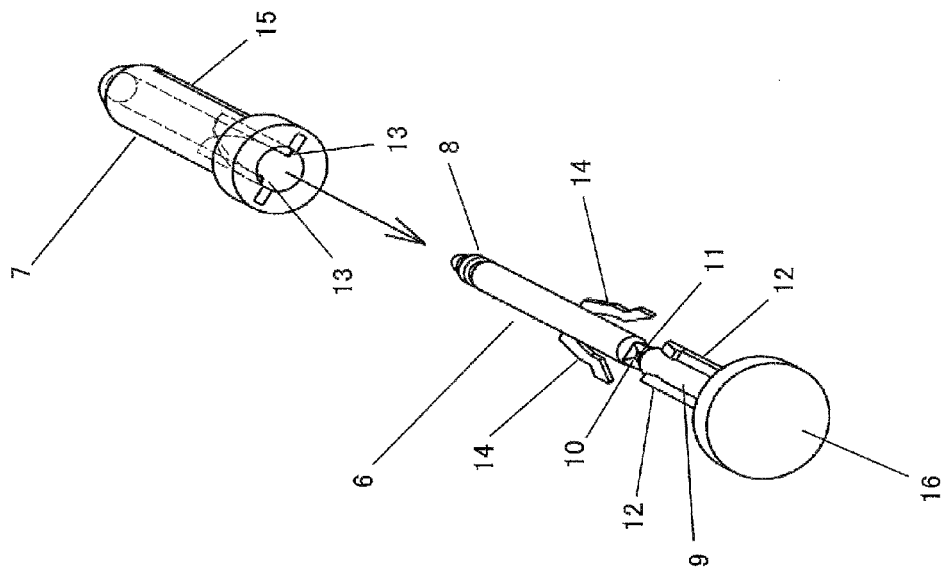
FIG. 6
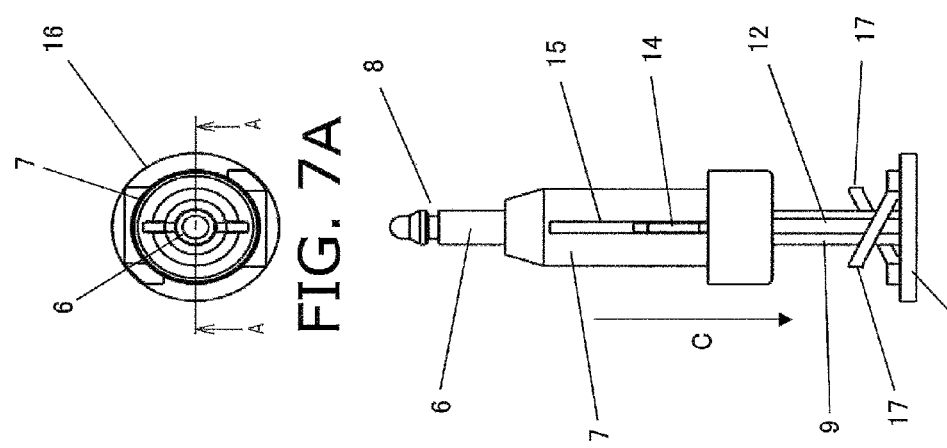
FIG. 7A
FIG. 7B

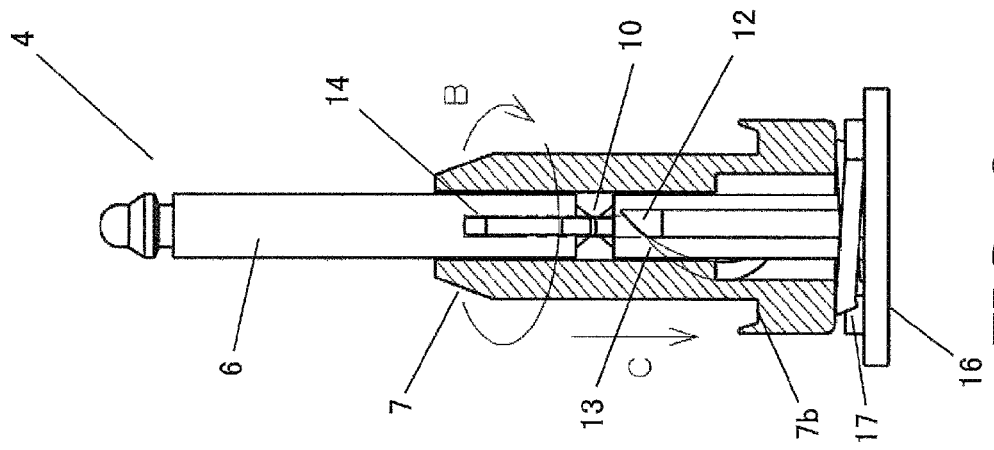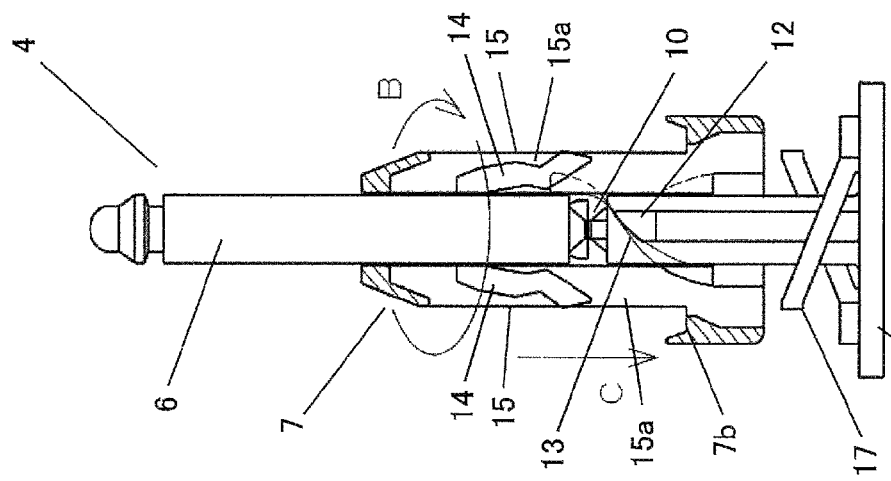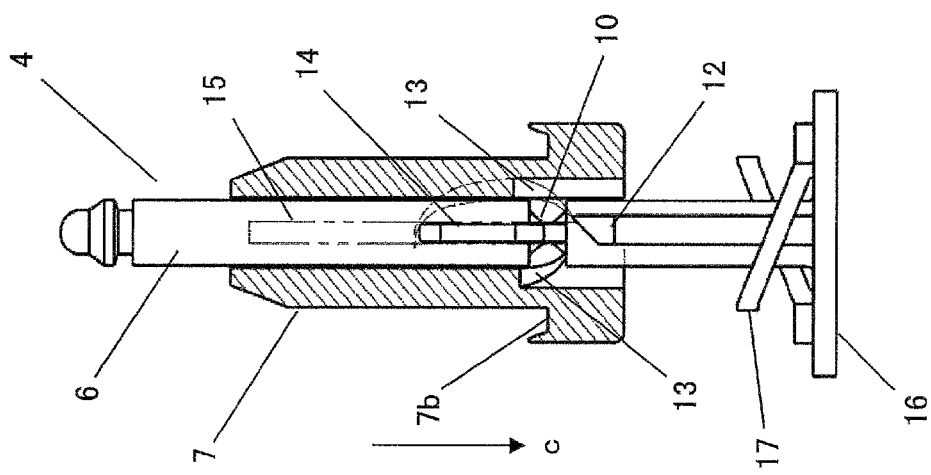

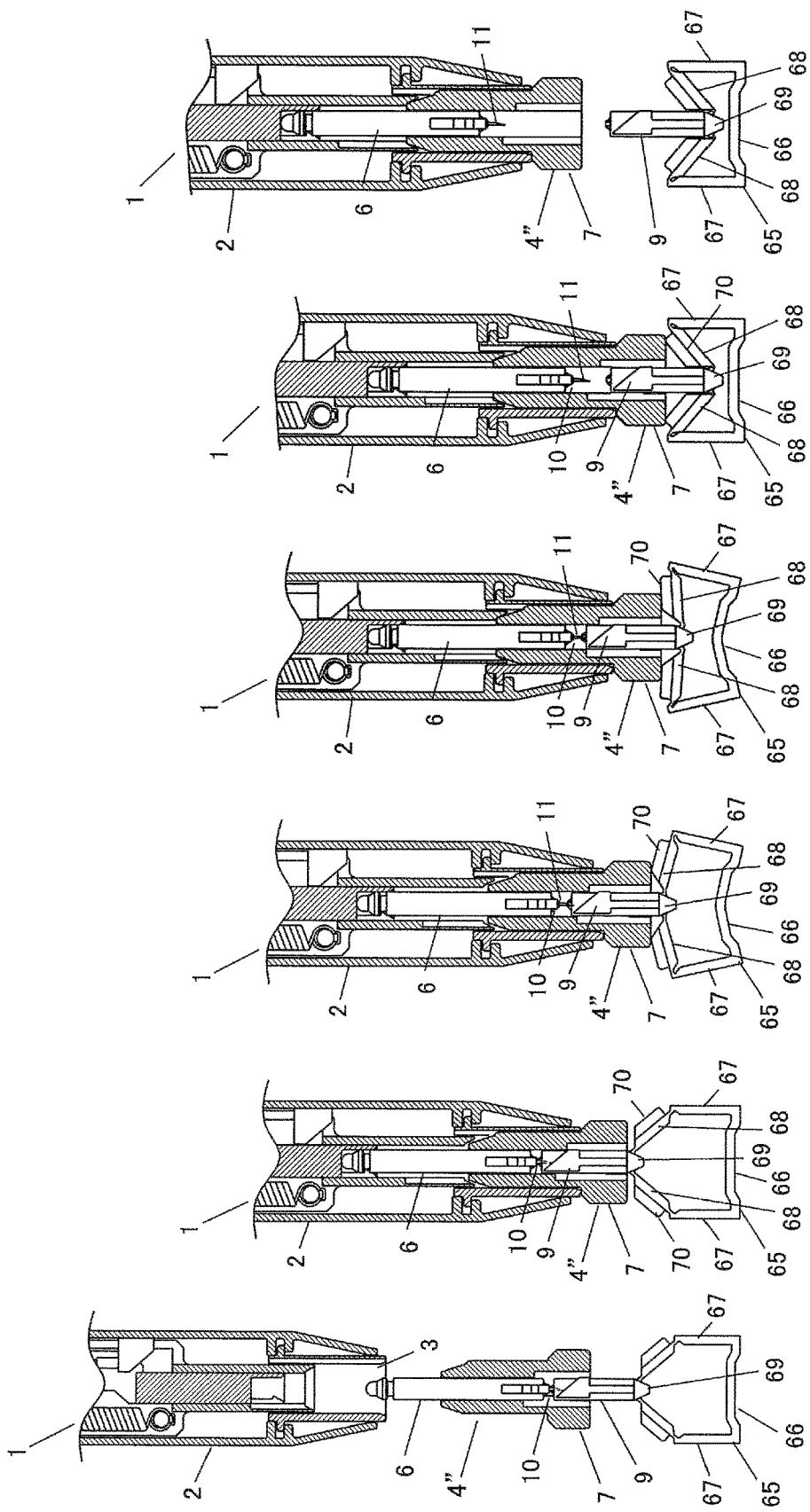

PUNCTURE INSTRUMENT, PUNCTURE NEEDLE CARTRIDGE MOUNTED IN PUNCTURE INSTRUMENT, AND METHOD FOR USING PUNCTURE INSTRUMENT AND PUNCTURE NEEDLE CARTRIDGE

PRIORITY

This application is a U.S. National stage application of International Application PCT/JP2013/006630, with an international filing date of Nov. 11, 2013, which claims priority to Japanese Patent Application No. 2012-261980 filed on Nov. 30, 2012, Japanese Patent Application No. 2012-277792 filed on Dec. 20, 2012, Japanese Patent Application No. 2013-157378 filed on Jul. 30, 2013, Japanese Patent Application No. 2013-157379 filed on Jul. 30, 2013 and Japanese Patent Application No. 2013-181085 filed on Sep. 2, 2013. The entire disclosures of International Application PCT/JP2013/006630, Japanese Patent Application No. 2012-261980, Japanese Patent Application No. 2012-277792, Japanese Patent Application No. 2013-157378, Japanese Patent Application No. 2013-157379, and Japanese Patent Application No. 2013-181085 are hereby incorporated herein by reference.

TECHNICAL FIELD

This disclosure relates to a puncture instrument that inserts a needle into a body and takes out blood, in order to measure a blood glucose level, for example, as well as to a puncture needle cartridge that is mounted to a puncture instrument and then discarded, and a method for using a puncture instrument and a puncture needle cartridge.

BACKGROUND

The following puncture instrument has been known in the past as this type of puncture instrument.

This puncture instrument has a tubular main case with an opening, a lancet holder provided inside this main case, a biasing member that biases this lancet holder toward a front end opening in the main case, a locking pawl that locks the lancet holder, a first manipulation button, and a second manipulation button. When the first manipulation button is pressed, the locking pawl is released and the lancet holder moves under the biasing of the biasing member toward the front end side of the main case. When the second manipulation button is pressed, the lancet is separated from the lancet holder.

When a user measures a blood glucose level, in the initial mounting operation, a puncture needle cartridge having a lancet is inserted into the opening of puncture instrument, and the lancet is mounted to the lancet holder of the puncture instrument. Then, in the puncture operation, the user executes puncture by pressing the first manipulation button of the puncture instrument. After this, the user presses the second manipulation button of the puncture instrument to release the lancet from the lancet holder, and the puncture cartridge is disengaged from the puncture instrument and discarded.

Thus, a series of puncture-related operations is performed (mounting operation, puncture operation, disposal operation) in the measurement of blood glucose levels (see Patent Literature 1, for example).
Patent Literature 1: Japanese Laid-Open Patent Application 2004-33440

SUMMARY

With a conventional puncture instrument, the initial mounting operation involves mounting a puncture needle cartridge to the puncture instrument, then, in the puncture operation, a user executes puncture by pressing a first manipulation button, and then, in the disposal operation, the user presses the second manipulation button to release the puncture needle cartridge. Because the puncture operation and the disposal operation are thus performed after the mounting operation, a puncture instrument equipped with first and second manipulation buttons is often misused by a person who is unaccustomed to handling puncture instruments, and improvement is needed in this area. With the puncture instruments that have been put to practical use so far, however, all of them have this configuration including first and second manipulation buttons. The reason for this is that the operation stroke for releasing the locking pawl with the first manipulation button is very different from the operation stroke for disengaging the lancet from the lancet holder with the second manipulation button, and this difference in the operation strokes makes it difficult for both puncture and lancet disposal to be performed with a single button.

As a result, puncture instruments still have two manipulation buttons, and so the user often mixes up the puncture operation and the disposal operation, making the job harder for the user. Also, in the mounting operation, the user holds the puncture needle cartridge in one hand, and holds the puncture instrument in the other hand, that is, the mounting operation requires the use of both hands, and this also makes the job harder. In other words, a conventional puncture instrument is inconvenient to use in performing the series of puncture-related operations (mounting operation, puncture operation, and disposal operation).

In view of this, this disclosure provides a puncture instrument and a puncture needle cartridge with which the series of puncture-related operations is easier to perform.

In one aspect of this disclosure, a puncture instrument has a first end side, which is the side on which a puncture needle cartridge is mounted, and a second end side opposite the first end side, the puncture instrument comprising a main case, a main rod, an injector rod, an actuating rod, a first biasing member, a manipulation component, and a locking member. The main case includes an opening on the first end side and on the second end side. The main rod is provided in the main case. The injector rod is mounted to the main rod and includes a lancet holder on the first end side. The actuating rod is mounted to the injector rod and includes an engagement component on the second end side. The first biasing member is configured to bias the injector rod toward the first end side. The manipulation component is provided slidably in and out of the opening on the second end side of the main case. The locking member is rotatably supported by a portion of the main rod between the injector rod and the manipulation component. The locking member includes a first engaged part configured to engage with the engagement component of the actuating rod, a second engaged part that abuts the portion of the manipulation component on the first end side, and a second biasing member configured to bias the first engaged part toward the engagement component.

In another aspect of this disclosure, a puncture needle cartridge has a first end side from which a puncture needle is stuck out, and a second end side opposite the first end side, and comprises a lancet main body, a puncture needle, a puncture needle cover, a connector, a lancet case, a guide protrusion, a spiral guide component, a slide protrusion, and a slide groove. The lancet main body includes a breakaway part in a middle thereof. The puncture needle is embedded in the lancet main body across the breakaway part of the lancet main body. The puncture needle cover is provided on the first end side of the lancet main body. The connector is a connector to the puncture instrument provided on the second end side of the lancet main body. The lancet case is mounted to an outer periphery of the lancet main body. The guide protrusion sticks out on the puncture needle cover. The spiral guide component is formed extending from the first end side of the lancet case toward the second end side, and configured to guide the guide protrusion so that the lancet case receives a turning force. The slide protrusion is formed more to the second end side than the breakaway part of the lancet main body, and protrudes outward. The slide groove is formed in the lancet case and configured to guide the slide protrusion.

The puncture instrument and puncture needle cartridge of this disclosure are effective at facilitating a series of puncture-related operations.

BRIEF DESCRIPTION OF THE DRAWINGS

FIG. 6 is an exploded oblique view of this puncture needle cartridge;

FIG. 7A is a top view of this puncture needle cartridge, and FIG. 7B is a front view of this puncture needle cartridge;

FIG. 9A is an A-A cross section of FIG. 7, FIG. 9B is an A-A cross section of FIG. 7 during operation, and FIG. 9C is an A-A cross section of FIG. 7 during operation;

FIGS. 27A, 27B, 27C, 27D, 27E and 27F are side views of the main components of this puncture needle cartridge and a puncture instrument.

DETAILED DESCRIPTION

Embodiments will now be described through reference to the drawings as needed. However, some unnecessarily detailed description may be omitted. For example, detailed description of already known facts or redundant description of components that are substantially the same may be omitted. This is to avoid unnecessary repetition in the following description, and facilitate an understanding on the part of a person skilled in the art.

The inventor has provided the appended drawings and the following description so that a person skilled in the art might fully understand this disclosure, but does not intend for these to limit what is discussed in the patent claims.

Embodiment 1

Figure 1:
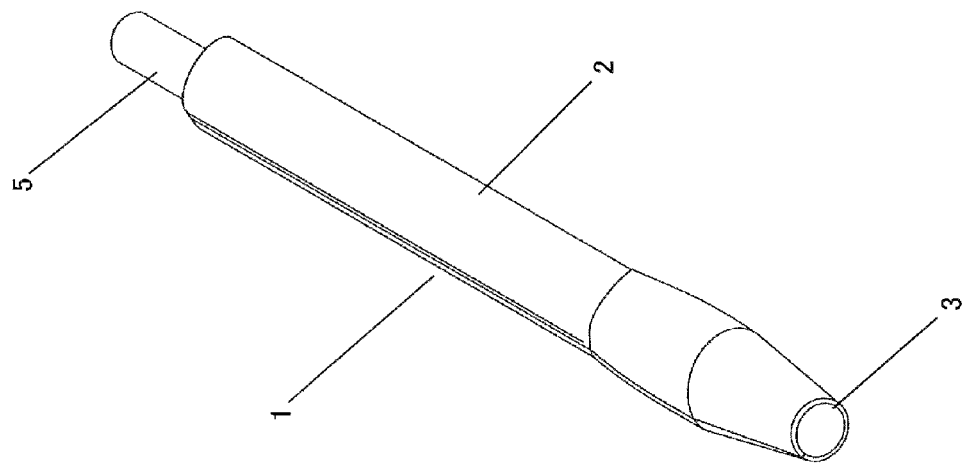
FIG. 1 is an oblique view of the puncture instrument pertaining to Embodiment 1.

FIG. 1 shows the puncture instrument 1 in this embodiment. For example, the puncture instrument 1 is a device for inserting a needle into a body and taking out blood in order to measure blood glucose levels. With this puncture instrument 1, puncture is performed after mounting the puncture needle cartridge 4 in FIG. 2 in the front end opening 3 of a long tubular main case 2. There are three operations related to this puncture: the mounting of the puncture needle cartridge 4, a puncture operation, and the disposal of the puncture needle cartridge 4.

Figure 3:
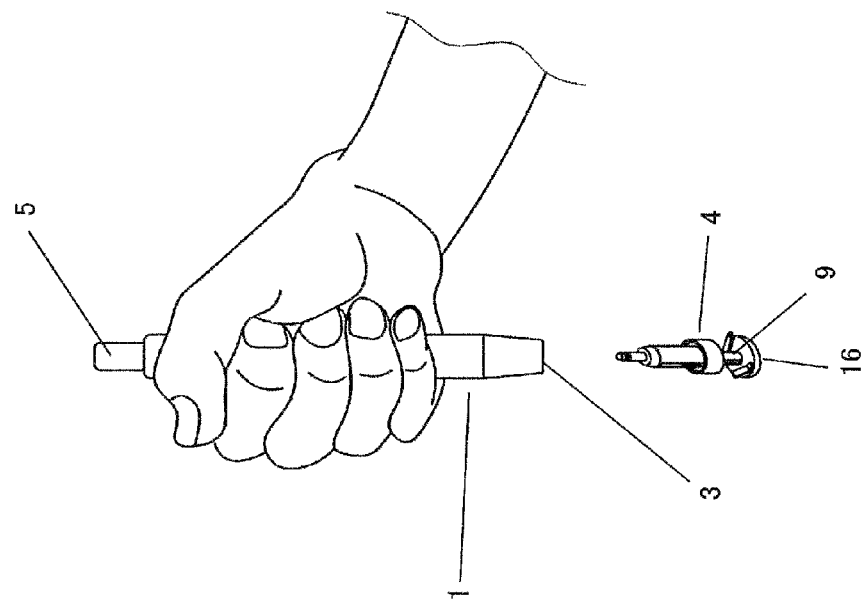
FIG. 3 shows the usage state of this puncture instrument.

In this embodiment, first, in the mounting operation (the first operation), as shown in FIG. 3, the user grips the puncture instrument 1 with the right hand, for example, and pushes the front end opening 3 of the puncture instrument 1 down toward the upright puncture needle cartridge 4. The puncture needle cartridge 4 is then mounted to the puncture instrument 1.

Figure 4:
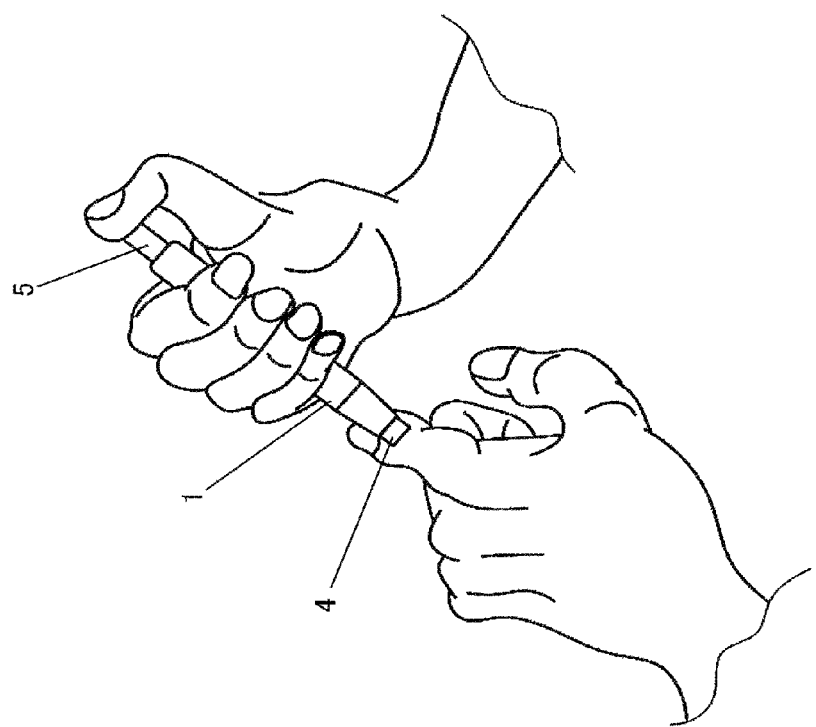
FIG. 4 shows the usage state of this puncture instrument.

Next, in the puncture operation (the second operation), as shown in FIG. 4, the user places the puncture needle cartridge 4 on a finger on his left hand, for example, and pushes a manipulation button 5 of the main case 2 with the thumb of the right hand gripping the puncture instrument 1. Puncture is carried out as a result, and blood flows out from the punctured site on the right thumb.

Finally, in the disposal operation (the third operation), as shown in FIG. 5, the user again presses the manipulation button 5 to disengage the puncture needle cartridge 4 from the puncture instrument 1, and the puncture needle cartridge 4 is discarded.

Thus, in this embodiment, the user can carry out the series of puncture-related operations (the mounting operation, the puncture operation, and the disposal operation) just by pressing a single button while holding the puncture instrument 1 in one hand. As a result, the puncture instrument 1 is extremely convenient to use, and this facilitates the series of puncture-related operations.

1-1 Configuration

The puncture needle cartridge 4 will now be described through reference to FIGS. 6 to 9, and then the puncture instrument 1 will be described through reference to FIGS. 10 to 12.

In the following description, unless otherwise stated, the puncture side of the puncture needle cartridge 4 will be referred to as the "front" side, and the opposite side from the puncture side will be referred to as the "rear" side.

1-1-1 Configuration of Puncture Needle Cartridge 4

As shown in FIG. 6, the puncture needle cartridge 4 is constituted by a lancet main body 6 that is substantially cylindrical in shape, a lancet case 7 that is substantially cylindrical in shape.

The substantially cylindrical lancet main body 6 is made of plastic, and has on its rear end side a connector 8 to the puncture instrument 1, on its front end side a cylindrical puncture needle cover 9, and in its middle a breakaway part 10. A puncture needle 11 (also shown in FIGS. 17 to 21) of the lancet main body 6 is embedded across the breakaway part 10 of the lancet main body 6. Furthermore, two (or more) guide protrusions 12 (an example of a guide protrusion) that stick out in the outer peripheral direction are provided at positions 180 degrees apart on the outer periphery of the puncture needle cover 9 of the lancet main body 6.

The tubular, plastic lancet case 7 is put over the cylindrical lancet main body 6 from the side of the connector 8 provided to the rear end of the lancet main body 6, and is mounted around the outer periphery of the middle part of the lancet main body 6 as shown in FIGS. 7A and 7B.

As shown in FIG. 6, spiral guide components 13 are formed on the inner face of the cylindrical lancet case 7, from the front end thereof toward the rear. Two (or more) of the guide components 13 are formed at positions 180 degrees apart on (just as are the guide protrusions 12), that is, at positions corresponding to the two guide protrusions 12 of the lancet main body 6 when the lancet case 7 has been mounted to the lancet main body 6. Since the guide components 13 are formed in a spiral shape, when the guide protrusions 12 of the lancet main body 6 are inserted into and guided by the guide components 13, the lancet case 7 receives the turning force with the guide protrusions 12.

Figure 8:
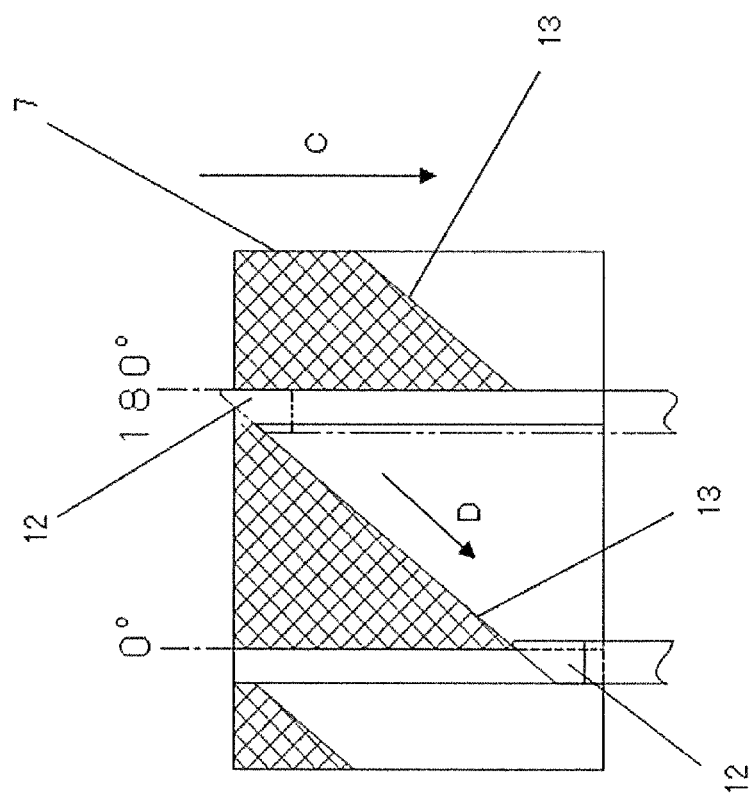
FIG. 8 is a development view of the main components of this puncture needle cartridge.

FIG. 8 is a development view of the inner face side of the lancet case 7, and shows the spiral guide components 13. The guide components 13 extend on the inner face of the tubular lancet case 7 from the front end of the lancet case 7 toward the rear, at a spacing of 180 degrees. Accordingly, when the lancet case 7 is slid forward (in the arrow C direction in FIGS. 7 and 8), the spiral guide components 13 slide in the arrow D direction over the guide protrusions 12, generating a turning force around the lancet main body 6 in the lancet case 7.

Also, as shown in FIG. 6, two (or more) slide protrusions 14 that stick out in the outer peripheral direction are provided 180 degrees apart and to the rear of the breakaway part 10 of the lancet main body 6. Also, two (or more) slide grooves 15 that guide the sliding of the slide protrusions 14 in the longitudinal direction are provided 180 degrees apart on the lancet case 7. Accordingly, when the lancet case 7 slides forward, the two slide protrusions 14 slide to the rear through the slide grooves 15.

Figure 2:
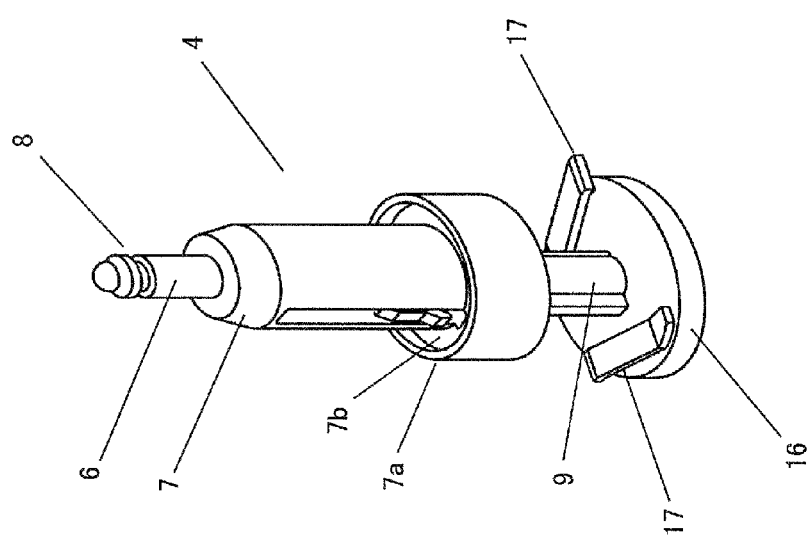
FIG. 2 is an oblique view of a puncture needle cartridge mounted to this puncture instrument.

As shown in FIG. 2, an annular recess 7a that opens toward the connector 8 side is provided to the outer peripheral part on the front end side of the lancet case 7. An annular contact face 7b is provided on the bottom of this recess 7a. The contact face 7b is substantially perpendicular to the axial direction of the lancet case 7.

In the mounting of the puncture needle cartridge 4, when the front end of the puncture instrument 1 is inserted into the annular recess 7a, the front end pushes on the contact face 7b, and the lancet case 7 is slid forward (the arrow C direction in FIG. 9) as shown in FIG. 9A. As shown in FIGS. 9A and 9B, the spiral guide components 13 slide over the guide protrusions 12 on the inner face side of the lancet case 7 at this point, and this generates a clockwise (arrow B direction) turning force on the lancet case 7. That is, when the lancet case 7 slides forward, it rotates clockwise around the lancet main body 6.

FIG. 9B shows the state when the lancet case 7 has rotated 90 degrees clockwise from the state in FIG. 9A, and FIG. 9C shows the state after 180 degrees of rotation.

This turning force on the lancet case 7 twists and breaks the breakaway part 10 of the lancet main body 6, exposing the puncture needle 11.

More specifically, the clockwise rotation of the lancet case 7 causes clockwise rotation of the slide protrusions 14 of the lancet main body 6 in contact with the slide wall faces 15a of the slide grooves 15 shown in FIG. 9B. These slide protrusions 14 rotate clockwise more to the rear (the upper side in FIGS. 9A to 9C) than the breakaway part 10 of the lancet main body 6. On the other hand, as shown in FIGS. 9B and 9C, the forward sliding of the lancet case 7 causes its spiral guide components 13 to push on the guide protrusions 12 of the lancet main body 6, and the side ahead of the breakaway part 10 of the lancet main body 6 (the lower side in FIGS. 9A to 9C) rotates counter-clockwise (the opposite direction from the rotation direction of the guide components 13; the opposite direction from the arrow B direction). Therefore, when the lancet case 7 slides forward, the breakaway part 10 in which the puncture needle 11 is embedded is subjected to rotational force in the reverse direction by the connecting portions ahead of and behind it, starts to be twisted off from the state in FIG. 9A, and breaks in a state of transition from FIG. 9B to 9C.

Specifically, with the puncture needle cartridge 4 in this embodiment, as the puncture needle cartridge 4 is mounted to the puncture instrument 1, the side to the rear of the breakaway part 10 of the lancet main body 6 inside the puncture needle cartridge 4 is rotated clockwise, and the front side is rotated counter-clockwise. The puncture needle cartridge 4 itself has this rotation mechanism for breaking the breakaway part 10 by two rotations in opposite directions. Therefore, the user can mount the puncture needle cartridge 4 to the puncture instrument 1 with the connector 8 merely by holding the puncture instrument 1 in one hand and pushing the front end opening 3 down toward the upright puncture needle cartridge 4, and this also generates a force in the opposite direction in the connecting portions ahead of and behind the breakaway part 10, so the breakaway part 10 can be reliably broken.

Therefore, the puncture needle cover 9 can be easily removed from the puncture needle cartridge 4, and the puncture needle 11 can be exposed from the lancet main body 6. As a result, the subsequent puncture operation can be carried out properly.

Also, as discussed above, during the mounting operation, the puncture needle cartridge 4 itself rotates the portions ahead of and behind the breakaway part 10 in opposite directions, so the puncture needle cartridge 4 merely needs to be set upright, and there is no need to fix the puncture needle cartridge 4 in place. This makes the device very convenient to use.

As shown in FIG. 2, the lancet main body 6 also has a disk-shaped base component 16 at its front end. This base component 16 is provided with two leaf springs 17 (an example of an elastic member) at opposing portions of the front end of the lancet case 7, with the cylindrical puncture needle cover 9 in between. The two leaf springs 17 are provided integrally with the base component 16. Therefore, when the mounting operation is finished, as shown in FIG. 9C, the breakaway part 10 is in a completely twisted state, and the two leaf springs 17 of the base component 16 have stored energy by being sandwiched between the base component 16 and the front end of the lancet case 7. The leaf springs 17 at this point push the base component 16 up and to the rear (upward in FIGS. 9A to 9C). This upward pushing tells the user that the mounting of the puncture needle cartridge 4 is finished, and also guides the user to the next operation, namely, lifting up the depressed puncture instrument 1, which makes the device very convenient to use.

Figure 17:
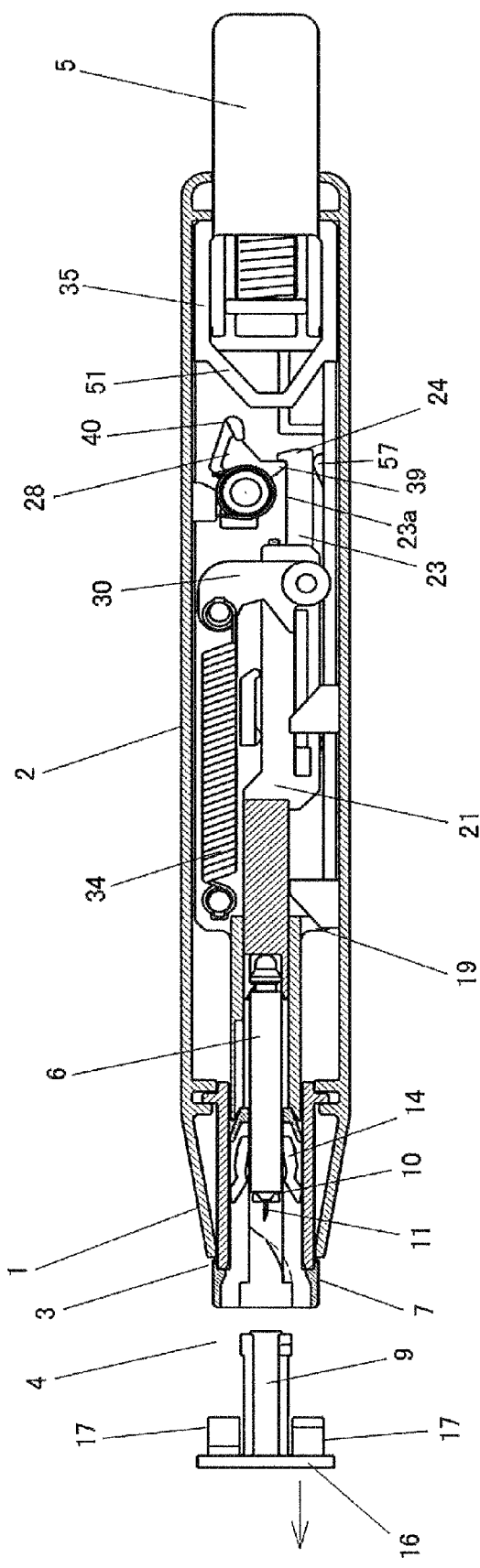
FIG. 17 is a cross section of this puncture instrument.

When the user lifts up the puncture instrument 1, the stored energy of the leaf springs 17 of the base component 16 is released, and this released energy causes the puncture needle cover 9 to spring away from the breakaway part 10 that has already been twisted off, as shown in FIG. 17. This exposes the puncture needle 11 at the front end part of the lancet main body 6.

Since the puncture needle cover 9 can thus be removed automatically, the puncture needle cartridge 4 is also more convenient to use in this respect.

The base component 16 in this embodiment is configured to be larger than the puncture needle cover 9 (that is, the base component 16 has a cross sectional area that is greater than that of the puncture needle cover 9 in a direction that intersects the axis of the lancet main body 6, so the puncture needle cartridge 4 can be stably put upright, and this facilitates the mounting operation.

1-1-2 Configuration of Puncture Instrument 1

The puncture instrument 1 to which the puncture needle cartridge 4 is mounted will now be described.

Figure 10:
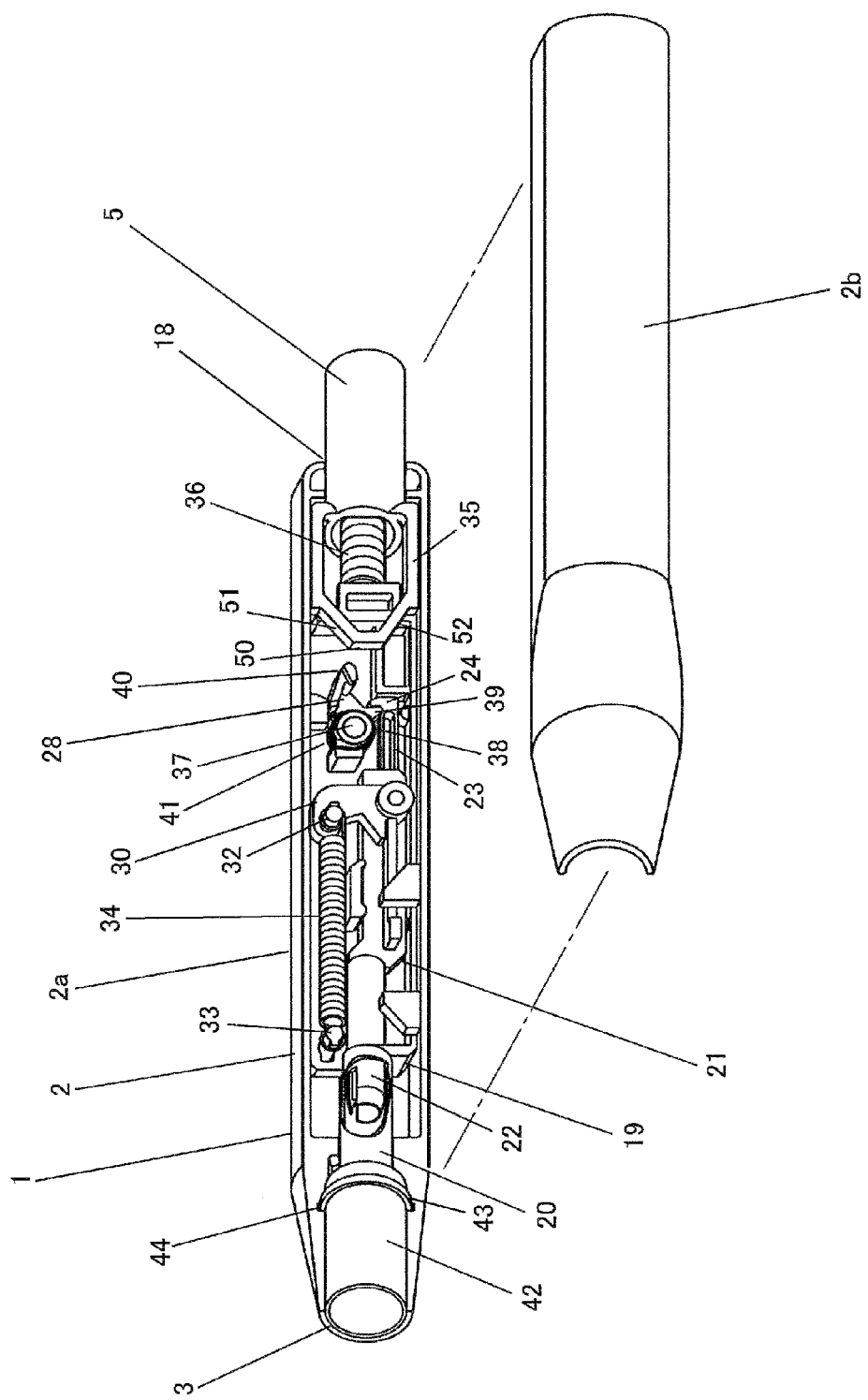
FIG. 10 is an exploded oblique view of this puncture instrument.

FIG. 10 is a diagram of the tubular puncture instrument 1, exploded in the axial direction.

The main case 2 of the puncture instrument 1 in this embodiment is substantially tubular in shape, having the front end opening 3 and a rear end opening 18, and is made up of a case piece 2a and a case piece 2b. The parts housed in this main case 2 will be described through reference to FIG. 11.

The largest of the parts housed in the main case 2 is a main rod 19 that has a holder insertion tube 20 (an example of a holder insertion tube) on the front end side. An injector rod 21 that has a lancet holder 22 is mounted on the front side (the left side in FIG. 11) of the main rod 19. The injector rod 21 has on its front end side the cylindrical lancet holder 22 to which the lancet main body 6 of the puncture needle cartridge 4 in FIG. 2 is mounted.

A slender actuating rod 23 is mounted on the case piece 2a side of this injector rod 21. The actuating rod 23 has a locking pawl 24 (an example of an engagement component) on the rear end side.

Figure 12:
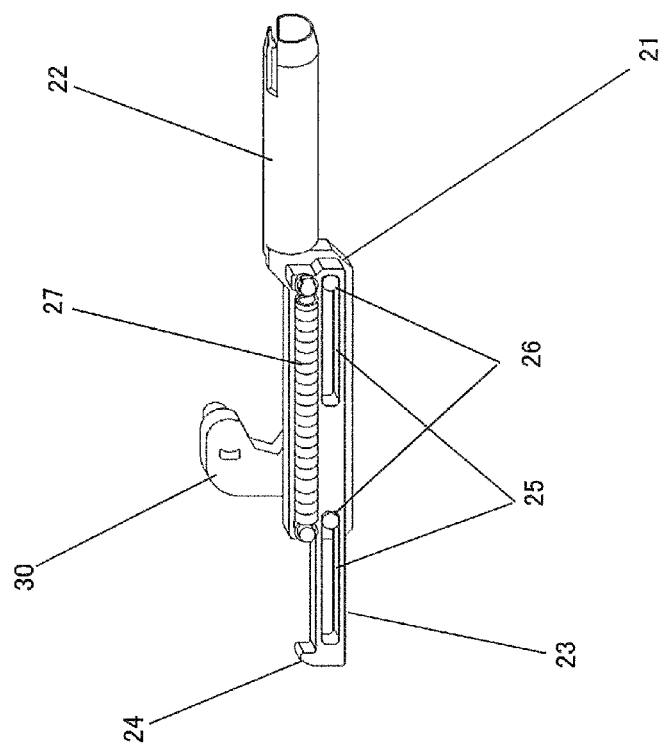
FIG. 12 is an oblique view of the main components of this puncture instrument.

FIG. 12 shows the state when the actuating rod 23 has been mounted to the injector rod 21, as seen from the case piece 2a side.

The injector rod 21 in this embodiment allows the actuating rod 23 to be mounted slidably in the longitudinal direction of the main case 2. Also, the actuating rod 23 is biased by an actuating spring 27 (an example of a third biasing member) toward a locking member 28 in FIG. 10. More precisely, two slots 25 (extending in the longitudinal direction) are provided to the front and rear end sides of the actuating rod 23, and these slots 25 are engaged with two shafts 26 of the injector rod 21, which allows the actuating rod 23 to slide in the longitudinal direction of the main case 2. Also, the front end part of the actuating rod 23 and the rear end part of the injector rod 21 are linked by the actuating spring 27, and the actuating rod 23 is biased to the rear, that is, in the direction of the locking member 28 in FIG. 10.

Figure 11:
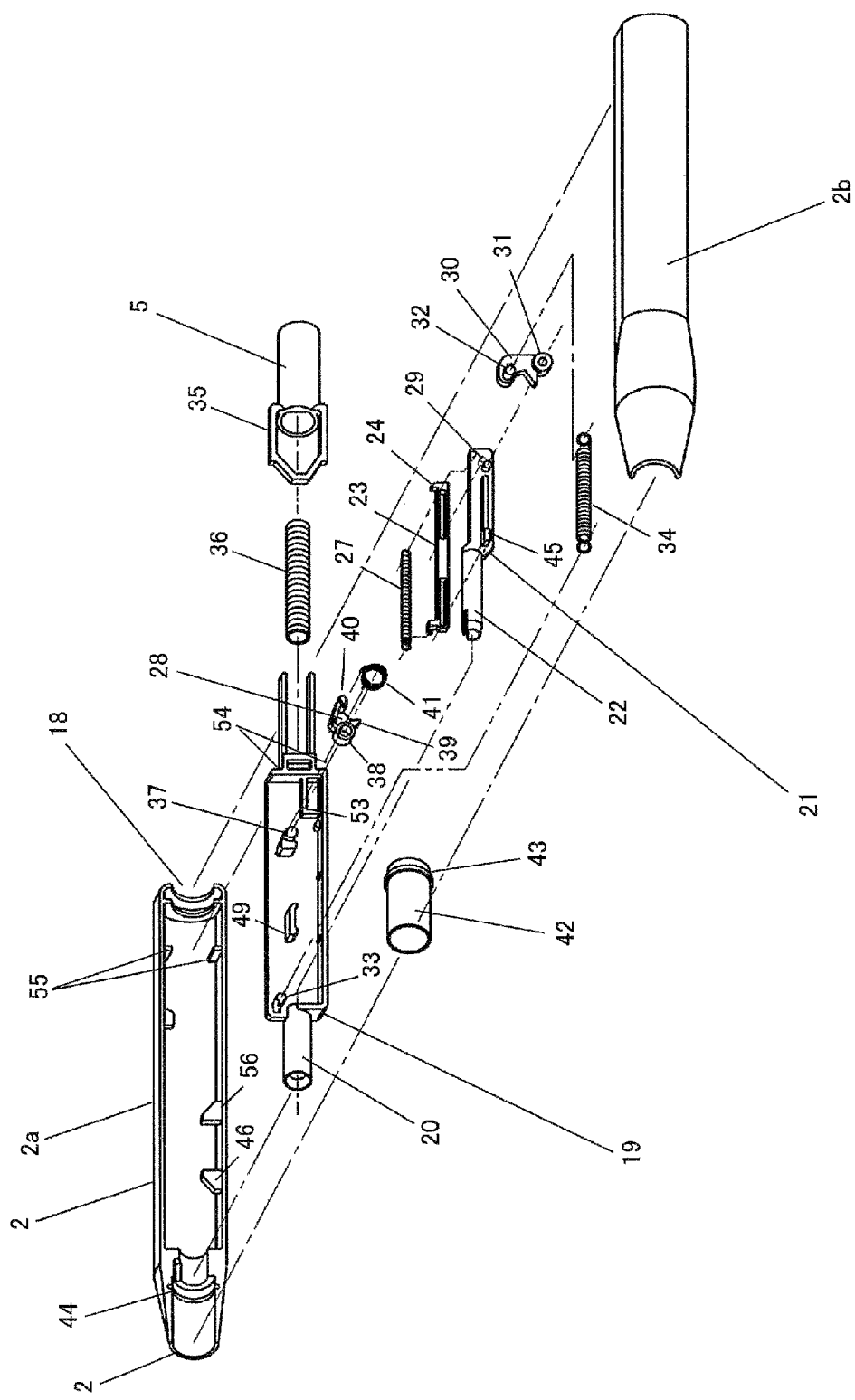
FIG. 11 is an exploded oblique view of this puncture instrument.

Also, as shown in FIG. 11, a shaft support 31 of a puncture cam 30 is mated with a shaft 29 on the rear end side of the injector rod 21, on the case piece 2b side.

As shown in FIG. 10, when the lancet holder 22 on the front end side of the injector rod 21 is inserted into the holder insertion tube 20 of the main rod 19, the injector rod 21 is supported slidably in the longitudinal direction of the main case 2 by the main rod 19. In FIG. 10, part of the holder insertion tube 20 is shown cut away to make it easier to see the state on the distal end side of the lancet holder 22 inserted into the holder insertion tube 20.

A main spring 34 (an example of a first biasing member) that biases the injector rod 21 to the front side of the main case 2 (the front end opening 3 side) is provided to the main rod 19. More precisely, a shaft 32 is provided to the puncture cam 30 on the injector rod 21, this shaft 32 and a shaft 33 on the front end side of the main rod 19 are linked by the main spring 34, and the injector rod 21 is biased to the front side. Therefore, the injector rod 21 slides toward the front end opening 3 under the biasing force of the main spring 34, and this performs the puncture operation.

The main case 2 further comprises the manipulation button 5 (an example of a manipulation component) that is provided slidably in and out of the rear end opening 18 of the main case 2. The manipulation button 5 has a manipulation member 35 at its front end, and a button spring 36 is housed in the tubular part on the rear end side. With the manipulation button 5 in this embodiment, the manipulation member 35 is provided with a flat part 50 that hits a push-out tab 40 (an example of a second engaged component) of the locking member 28 in the middle part on the front end side. The flat part 50 is provided with an upward-sloped face 51 and a downward-sloped face 52 that are adjacent and extend toward the rear. The upward-sloped face 51 and the downward-sloped face 52 are provided so that they are sloped with respect to the axis of the puncture instrument 1. Therefore, when the manipulation button 5 is operated, the locking member 28 on the front side can be manipulated with the manipulation member 35.

The locking member 28 is one of the characteristic parts in this embodiment, and the locking member 28 can be switched between the "puncture operation" and the "disposal operation" by manipulation of the manipulation button 5. More specifically, the locking member 28 is rotatably supported by a shaft 37 portion provided on the rear side of the main rod 19, between the manipulation button 5 and the injector rod 21. As shown in FIGS. 10, 11, and 13 to 21, locking member 28 is fan shaped, and has a shaft support 38 at the pivot portion of this fan shape. This shaft support 38 mates with the shaft 37 of the main rod 19 in a state in which the fan side is facing the manipulation button 5. As shown in FIGS. 10 and 11, the locking member 28 also has an engagement pawl 39 (an example of a first engaged component) that engages with the locking pawl 24 of the actuating rod 23, on the actuating rod 23 side (hereinafter also referred to as the fan bottom side) on the distal end side of the fan shape, and has the push-out tab 40 that hits the front end side of the manipulation button 5, on the opposite side from the actuating rod 23 (hereinafter also referred to as the fan top side) on the distal end side of the fan shape.

A locking member spring 41 (an example of a second biasing member) that biases the engagement pawl 39 of the locking member 28 toward the locking pawl 24 of the actuating rod 23 (the clockwise direction in FIG. 10; hereinafter referred to as clockwise) is formed by a coil spring and attached to the shaft support 38 of the locking member 28.

In FIG. 10, the engagement pawl 39 of the locking member 28 is engaged with the locking pawl 24, and sliding (shooting) of the injector rod 21 toward the front is locked. The user switches between the puncture operation and the disposal operation by rotating this locking member 28, and this switching operation will be described in detail below.

A cylindrical bushing 42 is mounted rotatably around the axis of the main case 2 on the front end side of the main case 2. More specifically, a rotary ring 43 provided on the rear side of the bushing 42 is inserted into a groove 44 of the main case 2 and rotatably mounted to the main case 2. The holder insertion tube 20 of the main rod 19 is inserted into this bushing 42.

The case piece 2a and the case piece 2b are fitted together in this state.

1-2 Operation

The "mounting operation" for the puncture instrument 1 and the puncture needle cartridge 4 having the above configuration will now be described mainly through reference to FIGS. 13 to 17, then the "puncture operation" will be described mainly through reference to FIG. 18, and then the "disposal operation" will be described mainly through reference to FIGS. 19 to 21.

1-2-1 Mounting Operation

Figure 13:
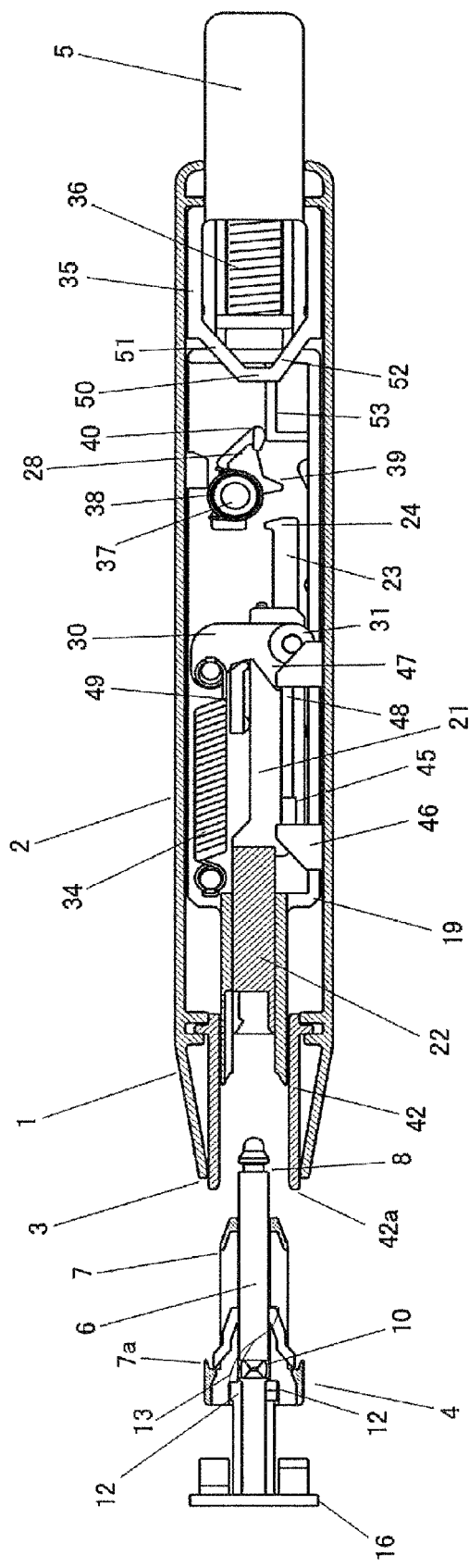
FIG. 13 is a cross section of this puncture instrument.

FIG. 13 shows the initial state of the main case 2. This initial state is a state in which, as shown in FIG. 3, the user holds the puncture instrument 1 and has not yet pushed the puncture instrument 1 down toward the upright puncture needle cartridge 4.

Before the rear side of the puncture needle cartridge 4 is inserted into the main case 2 from the front end opening 3 of the puncture instrument 1, inside the main case 2 the main rod 19 is pushed forward by the button spring 36 housed in the manipulation button 5. As a result, the main rod 19 stops at the position where a case stopper contact part 45 of the injector rod 21 mounted to the main rod 19 is in contact with a front case stopper 46 of the main case 2. At this point, in the middle of the main rod 19, the main spring 34 pulls the puncture cam 30 of the injector rod 21 forward. Therefore, the puncture cam 30 rotates counter-clockwise around the shaft support 31 (in the counter-clockwise direction in FIG. 13; hereinafter referred to as counter-clockwise), and a stop tab 47 thereof hits and stops a rib 48 of the injector rod 21. The main spring 34 also pulls the injector rod 21 forward via the puncture cam 30. The injector rod 21 stops with respect to the main rod 19 at the position where the puncture cam 30 is in contact with a puncture cam stopper 49 of the main rod 19.

The main rod 19 in this embodiment has a lock piece lower stopper 53 (an example of a first stopper). When the locking member 28 which is axially supported to the rear of the main rod 19 is rotated in the clockwise direction (the biasing direction of the locking member spring 41), the lock piece lower stopper 53 stops the rotation at a position in which the push-out tab 40 of the locking member 28 is opposite the flat part 50 of the manipulation button 5. Therefore, the locking member 28 that has been rotated clockwise by the locking member spring 41 stops when the push-out tab 40 on the fan top side hits the lock piece lower stopper 53.

Figure 14:
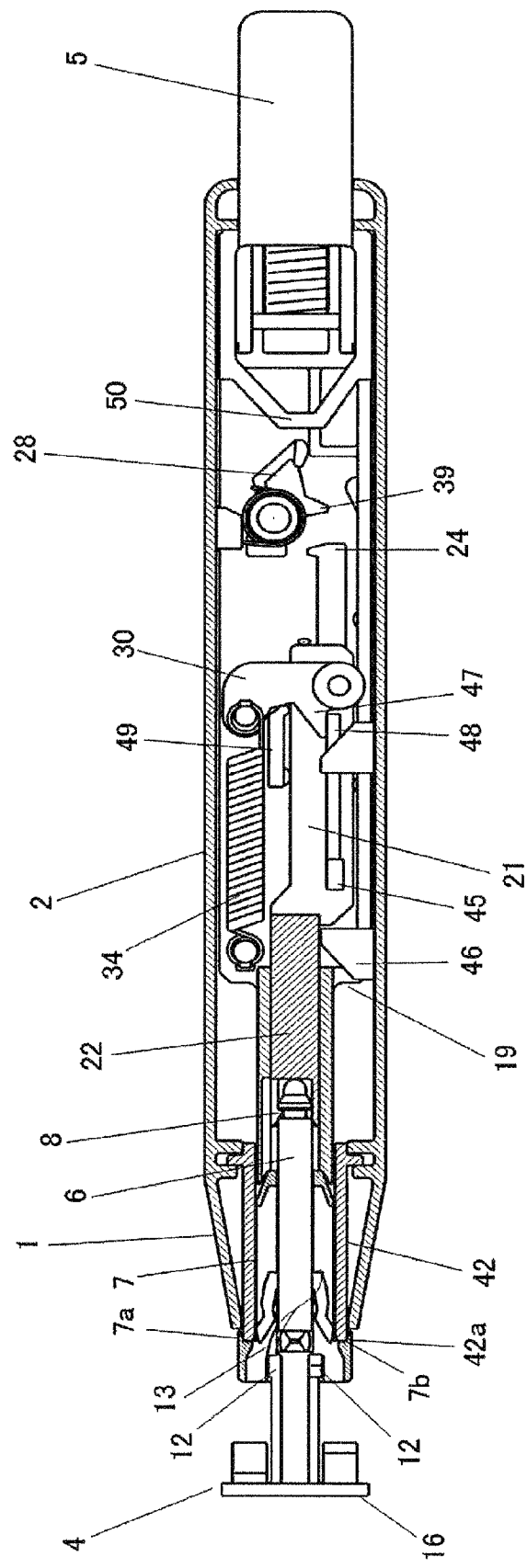
FIG. 14 is a cross section of this puncture instrument.

FIG. 14 shows the state when the puncture needle cartridge 4 has been pushed into the main case 2. The state of the puncture needle cartridge 4 in FIG. 14 corresponds to FIG. 9A.

When the puncture needle cartridge 4 is pushed into the main case 2, the lancet main body 6 is engaged with the lancet holder 22 of the injector rod 21 by its connector 8. Consequently, the puncture needle cartridge 4 is mounted to the puncture instrument 1. When the puncture needle cartridge 4 is pushed further into the main case 2, the lancet main body 6 pushes the injector rod 21 toward the rear. When the injector rod 21 pushes the main rod 19 toward the rear via the puncture cam 30 and the main spring 34, the main rod 19 stops when its rear end 54 hits a main rod stopper 55 of the main case 2 (FIG. 11). This results in the state shown in FIG. 14. When the injector rod 21 is pushed in further, the injector rod 21 slides rearward through the stopped main rod 19. Therefore, the puncture cam 30 of the injector rod 21 stretches the main spring 34, the puncture force (that is, the injection force used for puncture) is stored in the main spring 34.

Meanwhile, the twisting off of the breakaway part 10 is commenced at the puncture needle cartridge 4. More specifically, on the front end side of the main case 2, an annular pushing face 42a provided to the front end of the bushing 42 is inserted into the annular recess 7a of the lancet case 7 and hits the annular contact face 7b shown in FIG. 2. When the puncture needle cartridge 4 is then pushed into the main case 2, the pushing face 42a of the bushing 42 pushes the contact face 7b, and slides the lancet case 7 toward the base component 16. This sliding, as discussed above, causes the guide components 13 on the inner face of the lancet case 7 to slide in a spiral over the guide protrusions 12. As a result, a force in the opposite direction is generated at the connecting portions ahead of and behind the breakaway part 10 of the lancet main body 6, and the twisting off of the breakaway part 10 is commenced.

The bushing 42 also rotates along with the rotation of the lancet case 7.

Figure 15:
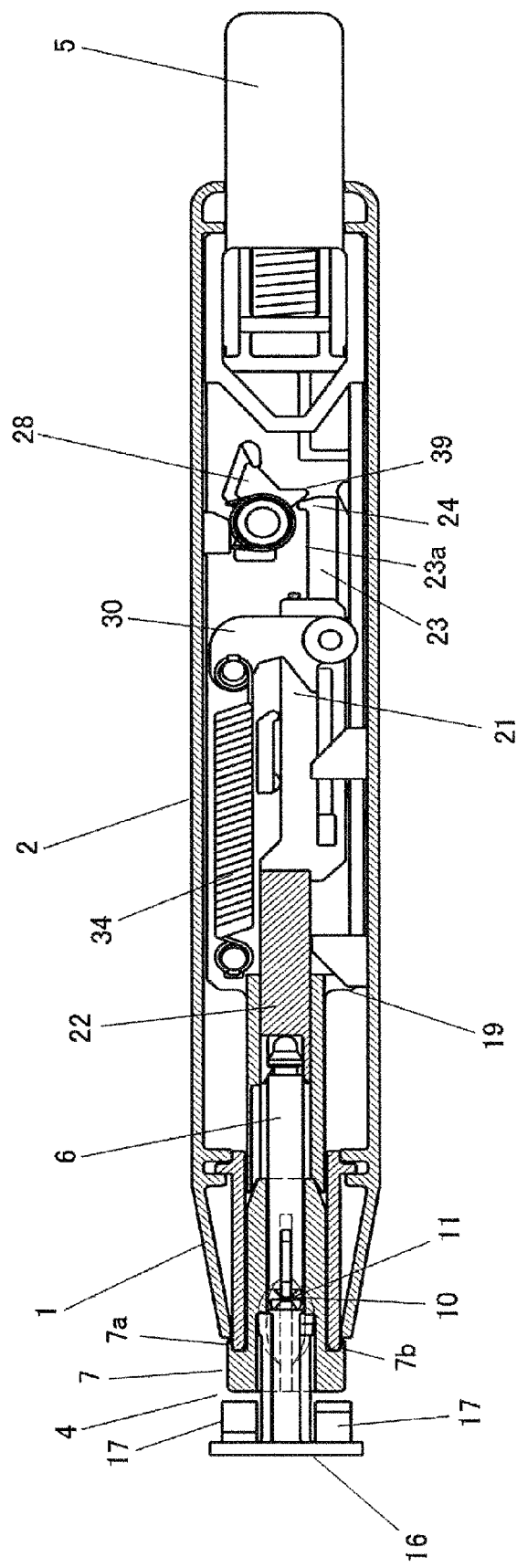
FIG. 15 is a cross section of this puncture instrument.

FIG. 15 shows a state in which the lancet case 7 has been turned 90 degrees with respect to the lancet main body 6 (the state in FIG. 9B). At this point, the breakaway part 10 of the puncture needle cartridge 4 is just about to be twisted off. At the puncture instrument 1, the injector rod 21 moves further to the rear, and the locking pawl 24 on the rear side of the actuating rod 23 hits the engagement pawl 39 of the locking member 28. The actuating rod 23 in this embodiment rotates the engagement pawl 39 of the locking member 28 with the locking pawl 24 on its rear end side, in the opposite direction from the biasing direction of the locking member spring 41. After this rotation, the engagement pawl 39 is prevented from being rotated in the biasing direction by the locking member spring 41 by the face of the actuating rod 23 opposite the engagement pawl 39 of the locking member 28, that is, an anti-rotation component 23a (an example of an anti-rotation component). Therefore, when the injector rod 21 moves rearward from the state shown in FIG. 15, the locking pawl 24 pushes up the engagement pawl 39 on the fan bottom side of the locking member 28, and the engagement pawl 39 rotates counter-clockwise. After this, as shown in FIG. 16, when the locking pawl 24 pushes past the engagement pawl 39, the engagement pawl 39 attempts to rotate clockwise, but stops its rotation upon hitting the anti-rotation component 23a of the actuating rod 23.

Figure 16:
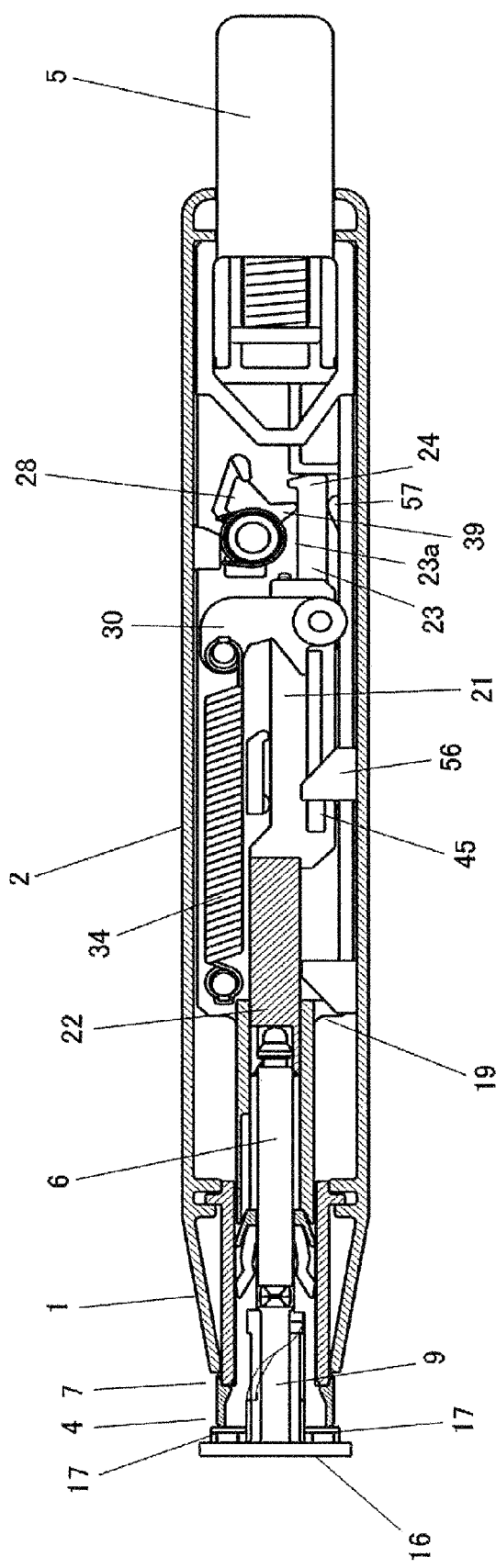
FIG. 16 is a cross section of this puncture instrument.

FIG. 16 shows the state when the lancet case 7 has been turned 180 degrees with respect to the lancet main body 6 (the state in FIG. 9C). The injector rod 21 slides rearward through the stopped main rod 19, and stops when its case stopper contact part 45 hits a rear case stopper 56 of the main case 2. At this point, the main spring 34 is stretched as far as it goes, and the puncture force is stored.

At the puncture needle cartridge 4, the breakaway part 10 is completely twisted off. Also, the two leaf springs 17 of the base component 16 are flanked by the base component 16 and the front end of the lancet case 7 in a state of having stored energy.

FIG. 17 shows the completion of the mounting operation of the puncture needle cartridge 4. When the user lifts up the depressed puncture instrument 1, the stored energy of the leaf springs 17 of the base component 16 is released. This released energy causes the puncture needle cover 9 to snap away from the breakaway part 10 that has already been twisted off. As a result, the puncture needle 11 can be exposed at the front end portion of the lancet main body 6.

Specifically, in the mounting operation, when the user holds the puncture instrument 1 in one hand and pushes it down toward the upright puncture needle cartridge 4, at the puncture instrument 1 a puncture force is stored in the main spring 34, and at the puncture needle cartridge 4 the breakaway part 10 is broken. After this, when the puncture instrument 1 is lifted up, the puncture needle cover 9 is removed and the puncture needle 11 is exposed. Therefore, the user can carry out the mounting of the puncture needle cartridge 4 simply by holding the puncture instrument 1 in one hand, pushing it down toward the puncture needle cartridge 4, and then lifting it up again.

When the user lifts up the puncture instrument 1, the pushing force on the injector rod 21 by the puncture needle cartridge 4 goes away, and the injector rod 21 is pulled forward by the main spring 34. Therefore, the locking pawl 24 of the actuating rod 23 also moves forward from the state in FIG. 16, forming a locked state in which the locking pawl 24 and the engagement pawl 39 are engaged, as shown in FIG. 17. This locked state stops the injector rod 21 from sliding (shooting) to the front end opening 3 side, and this completes the preparation for puncture. That is, when the engagement of the engagement pawl 39 and the locking pawl 24 is released, the locked state is unlocked, and the injector rod 21 is shot forward.

A protrusion 57 is provided to the main case 2 portion on the opposite side from the engagement pawl 39, flanking the actuating rod 23. The protrusion 57 supports the actuating rod 23.

1-2-2 Puncture Operation

Figure 18:
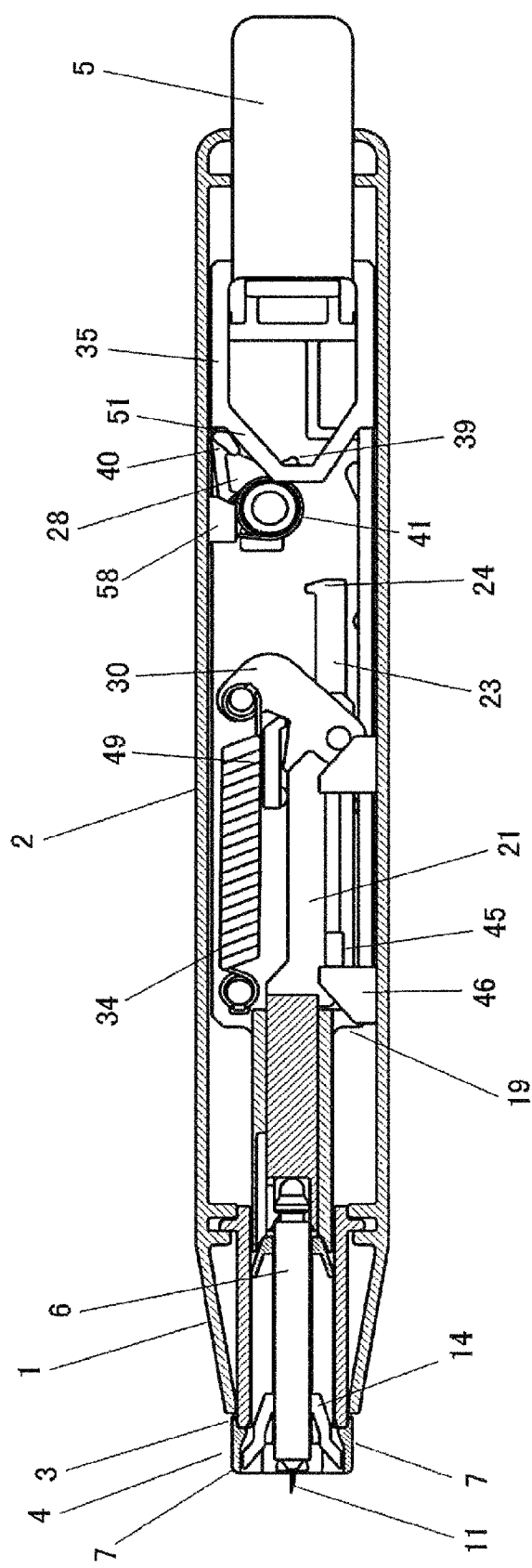
FIG. 18 is a cross section of this puncture instrument.

FIG. 18 shows the puncture operation. As shown in FIG. 17, the actuating rod 23 in this embodiment is such that when the locking pawl 24 of the actuating rod 23 is engaged with the engagement pawl 39 on the fan bottom side of the locking member 28, the push-out tab 40 on the fan top side of the locking member 28 is disposed at a position opposite the upward-sloped face 51 of the manipulation button 5.

Therefore, as shown in FIG. 18, when the user pushes (manipulates) the manipulation button 5 forward, the upward-sloped face 51 of the manipulation member 35 hits the push-out tab 40, which pushes up the push-out tab 40 and rotates the locking member 28 counter-clockwise. The engagement pawl 39 then rotates counter-clockwise and is disengaged from the locking pawl 24, which results in an unlocked state.

Once unlocked, the injector rod 21 is pulled by the main spring 34 and is forcefully shot to the front end opening 3 side. The injector rod 21 slides until the case stopper contact part 45 hits the front case stopper 46. On the front side of the puncture instrument 1, the puncture needle 11 of the lancet main body 6 engaged with the injector rod 21 is shot out from the front end of the puncture needle cartridge 4. As a result, the puncture needle 11 punctures the finger, etc., of the user.

During the sliding of the injection rod 21, the puncture cam 30 rotates clockwise while its middle part hits the puncture cam stopper 49, and this stretches out the main spring 34. At the next instant, the main spring 34 contracts again, and as a result the injection rod 21 is pulled to the rear end opening 18 side as shown in FIG. 19 after puncture, and the puncture needle 11 is pulled back into the lancet case 7.

Returning to FIG. 18, a lock piece upper stopper 58 (an example of a second stopper) is provided to the main case 2 in this embodiment. When the push-out tab 40 of the locking member 28 is rotated counter-clockwise (that is, in the opposite direction from that of the biasing force of the locking member spring 41) by the upward-sloped face 51 of the manipulation button 5, the lock piece upper stopper 58 stops this rotation in the opposite direction. Therefore, when the user further depresses the manipulation button 5, the push-out tab 40 rotates and hits the lock piece upper stopper 58. In this contact state, the manipulation button 5 cannot be pushed in any further, so the user can tell that puncture is finished. The user then stops pushing on the manipulation button 5, removes his finger from the manipulation button 5, and ends the puncture operation.

As discussed above, the user can easily carry out the puncture operation merely by pushing the manipulation button 5.

Furthermore, in this embodiment the puncture instrument 1 is configured so that the main case 2 is in the form of a long tube, the manipulation button 5, which is able to slide in and out of the rear end opening 18 of the main case 2, is provided on the axis of the main case 2, the manipulation button 5 is slid along the axis of the main case 2, and this performs the puncture operation. Therefore, as shown in FIG. 4, in a state in which the user has placed a finger on the puncture needle cartridge 4 during the puncture operation, the user can grip the tubular main case 2 with his palm in a stabilized manner and push the manipulation button 5 in toward the puncture position on the axis of the main case 2 from the stable state. As a result, the puncture needle cartridge 4 and the puncture instrument 1 in this embodiment can perform puncture in an extremely stable state, making the device very convenient to use.

1-2-3 Disposal Operation

Figure 19:
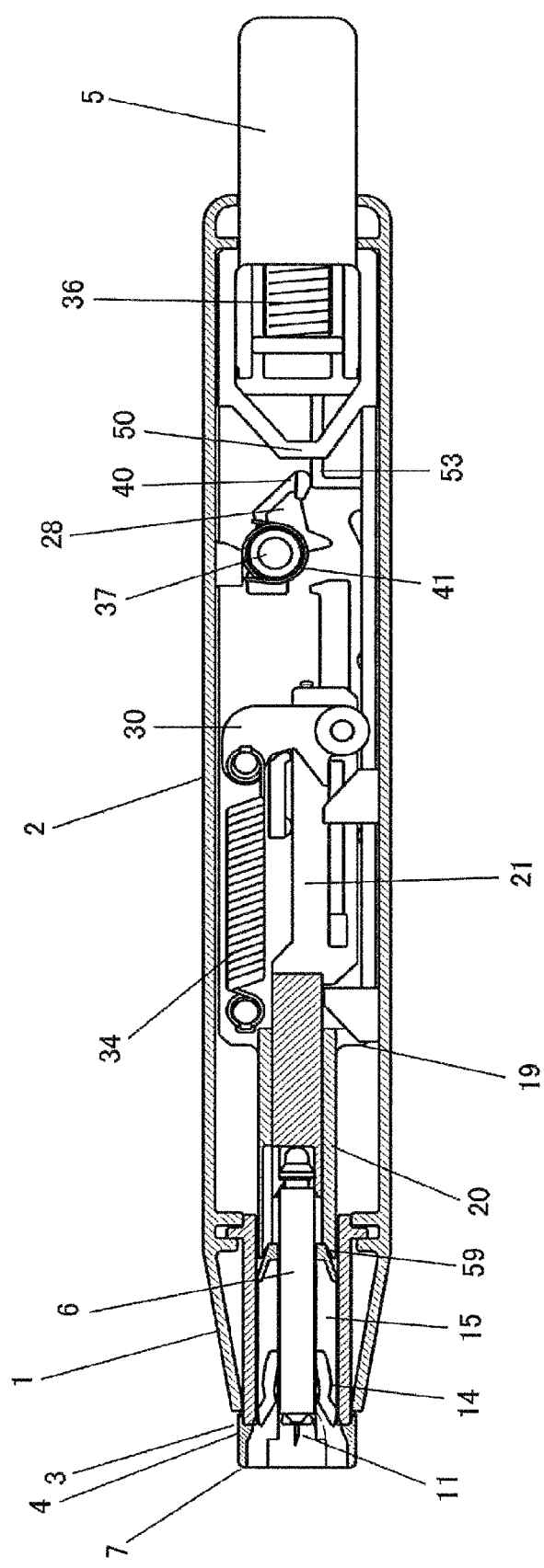
FIG. 19 is a cross section of this puncture instrument.

FIG. 19 shows the completed state of the puncture operation, and also shows the start of the disposal operation. When the user removes his finger from the manipulation button 5, the manipulation button 5 is returned to its position prior to the puncture operation by the return force of the button spring 36 housed inside. The main rod 19 in this embodiment is provided with the lock piece lower stopper 53 (an example of a stopper) that stops the rotation of the push-out tab 40 of the locking member 28 at a position opposite the flat part 50 of the manipulation button 5 when the locking member 28 is rotated clockwise (the biasing direction of the locking member spring 41). Therefore, the rotation of the push-out tab 40 of the locking member 28 is stopped by the lock piece lower stopper 53 at a position opposite the flat part 50 of the manipulation button 5. Consequently, when the manipulation button 5 is pressed in again, the manipulation member 35 can manipulate the locking member 28 with the flat part 50 via the push-out tab 40, as discussed below.

Figure 20:
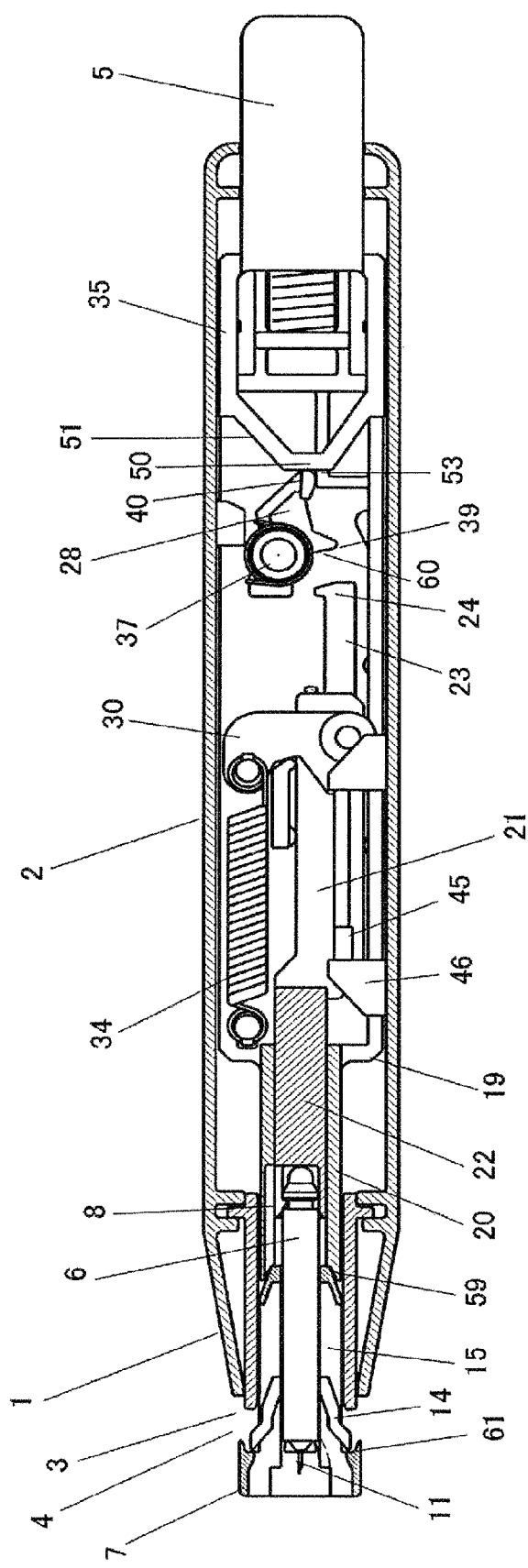
FIG. 20 is a cross section of this puncture instrument.

FIG. 20 shows the disposal operation for the puncture needle cartridge 4. The locking member 28 in this embodiment positions the shaft support 38 of the main rod 19 at a place corresponding to the upward-sloped face 51, which slopes up from the flat part 50 of the manipulation button 5. Therefore, when the manipulation button 5 is pressed, the flat part 50 of the manipulation member 35 hits the push-out tab 40 of the locking member 28. At this point, since the shaft support 38 is positioned more on the upward-sloped face 51 side than the contact portion between the flat part 50 and the push-out tab 40, the push-out tab 40 is biased to rotate clockwise. However, the rotation of this push-out tab 40 is stopped by abutting the lock piece lower stopper 53. Therefore, when the manipulation button 5 is pressed, the main rod 19 can be slid forward along with the locking member 28 via the shaft 37 of the locking member 28 and the push-out tab 40. The injection rod 21 is also pulled by the main spring 34 and slides forward along with the main rod 19.

The main rod 19 in this embodiment has provided on its front end side the holder insertion tube 20 that houses the lancet holder 22 of the injection rod 21. A lancet push-out face 59 (an example of a push-out face) is provided to the front end of the holder insertion tube 20. Therefore, when the main rod 19 slides forward, the lancet push-out face 59 hits the rear end of the lancet case 7 and can push the puncture needle cartridge 4 out of the main case 2. During this push-out operation, the case stopper contact part 45 of the injection rod 21 hits the front case stopper 46. As a result, the main rod 19 stops sliding with respect to the main case 2, and the actuating rod 23 mounted to the injection rod 21 also stops.

When the manipulation button 5 is pressed further, the main rod 19 and the locking member 28 slide forward, and the engagement pawl 39 on the fan bottom side of the locking member 28 hits the locking pawl 24 of the stopped actuating rod 23.

The locking member 28 in this embodiment is provided with a pressing face 60 (an example of a pressing face) that pushes the locking pawl 24 of the actuating rod 23 toward the front side of the main case 2, on the front face side of the engagement pawl 39 on the fan bottom side. Also, as discussed above, the actuating rod 23 is mounted slidably in the longitudinal direction of the main case 2 to the injection rod 21 in this embodiment. Also, this actuating rod 23 is biased by the actuating spring 27 in the direction of the locking member 28. Therefore, as shown in FIG. 21, even when the injection rod 21 is stopped, the pressing face 60 can push the locking pawl 24 and slide the actuating rod 23 forward. This allows the main rod 19 and the locking member 28 to continue sliding forward.

Figure 21:
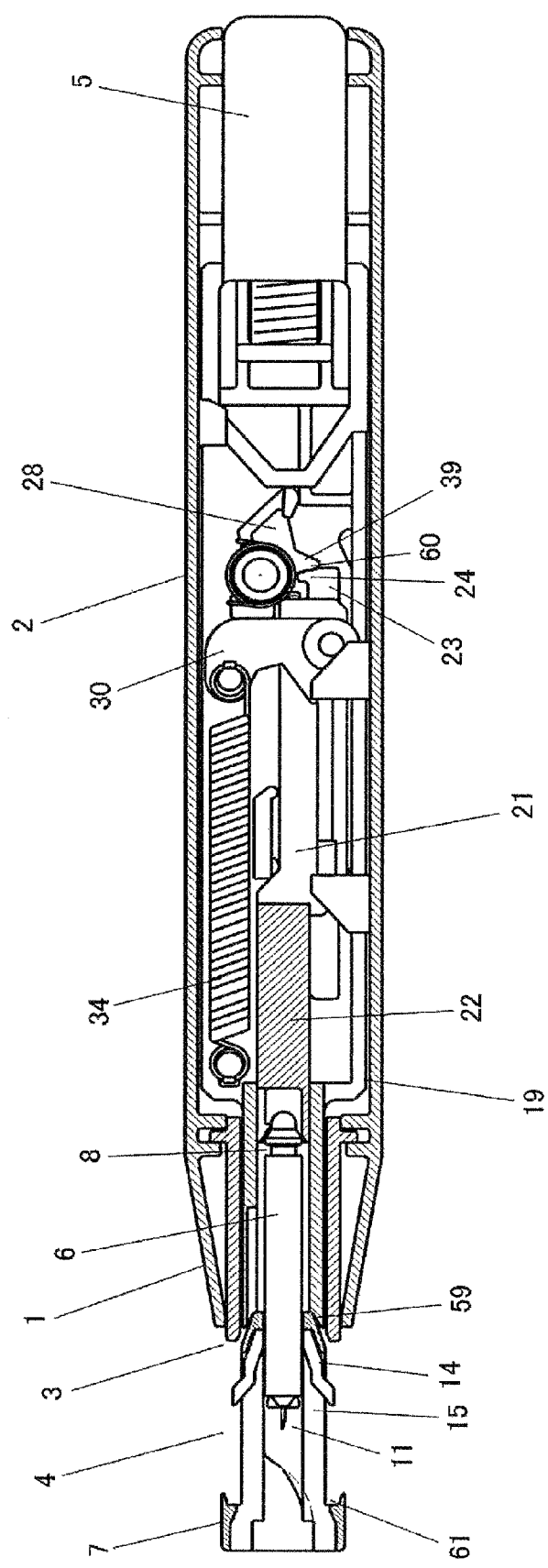
FIG. 21 is a cross section of this puncture instrument.

FIG. 21 shows the completed state of the disposal operation. When the manipulation button 5 is pressed further, the lancet push-out face 59 pushes the lancet case 7 forward on the front side of the main case 2. The lancet case 7 pulls the lancet main body 6 forward via the slide protrusions 14, and the connector 8 of the lancet main body 6 is pulled out of the lancet holder 22 of the stopped injection rod 21. When the lancet push-out face 59 then pushes the lancet case 7 completely out of the main case 2, the disposal operation is complete.

As discussed above, in this disposal operation, the user can discard the puncture needle cartridge 4 merely by pressing the manipulation button 5.

Figure 5:
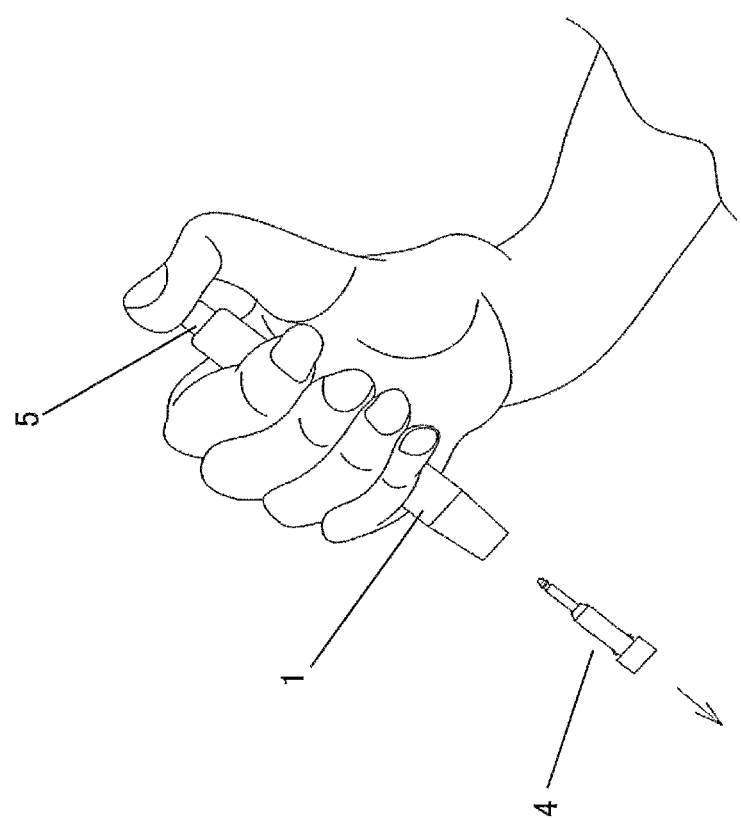
FIG. 5 shows the usage state of this puncture instrument.

After this, if the user removes his finger from the manipulation button 5, the return force of the main spring 34 pulls the main rod 19 back to the rear, returning to the initial state shown in FIG. 13. Specifically, with the locking member 28 in this embodiment, prior to the puncture operation the push-out tab 40 is disposed at a position opposite the upward-sloped face 51 of the manipulation member 35 as shown in FIG. 17, and prior to the disposal operation the push-out tab 40 is disposed at a position opposite the flat part 50 of the manipulation button 5. Therefore, the locking member 28 can switch the manipulation button 5 between two operations, namely, the puncture operation and the disposal operation. Therefore, as shown in FIGS. 3 to 5, once the user grasps the middle part of the main case 2, the mounting operation, puncture operation, and disposal operation of the puncture needle cartridge 4 can be performed in that same state, without the user changing his grip. Furthermore, the puncture operation and disposal operation can be carried out with just the manipulation button 5. As a result, a series of puncture-related operations can be performed with one hand, so the puncture instrument 1 is extremely easy to use, and this makes it easier to perform the series of puncture-related operations.

As shown in FIG. 17, with the puncture needle cartridge 4, prior to the puncture operation the slide protrusions 14 undergo elastic deformation and virtually entirely go into the slide grooves 15. When puncture is performed from this state as shown in FIG. 18, the distal ends of the slide protrusions 14 first come out forward from the slide grooves, and then are pulled rearward as shown in FIG. 19, and virtually the entire slide protrusions 14 go into the slide grooves 15 again. After this, as shown in FIG. 20, when the puncture needle cartridge 4 is ejected, the distal end sides of the slide protrusions 14 spread to outside the slide grooves 15, and the slide protrusions 14 slide through the slide grooves 15.

As shown in FIGS. 20 and 21, the lancet case 7 in this embodiment has a slide receiver 61 (an example of a slide receiver) on the forward inner peripheral part thereof, at a position that is posterior to the distal end of the lancet case 7 and is deeper inside than the distal end of the puncture needle 11. The slide receiver 61 hits the distal ends of the slide protrusions 14 of the lancet main body 6 when the lancet main body 6 has slid forward. Therefore, after the ejection of the puncture needle cartridge 4, the puncture needle 11 stops at the position where the distal ends of the slide protrusions 14 and the slide receiver 61 come into contact, and the puncture needle 11 does not protrude from the puncture needle cartridge 4.

1-3 Other Configuration and Operation

If a user who is not yet accustomed to the mounting of the puncture needle cartridge 4 performs the mounting operation in a state in which his thumb is on the manipulation button 5, the manipulation button 5 may end up being pushed in while the mounting operation is in progress. More specifically, as shown in FIG. 14, the manipulation button 5 on the rear side of the main case 2 may be pushed in when the lancet main body 6 on the front side is engaged with the injection rod 21 via the lancet holder 22. If this happens, the manipulation button 5 will slide the locking member 28 forward via the flat part 50 and the push-out tab 40, so the engagement pawl 39 of the locking member 28 will hit the locking pawl 24 on the front side, and the locking pawl 24 will be pushed in toward the injection rod 21. That is, the injection rod 21 will receive the force of the lancet main body 6 from the front, and receive the force of the manipulation button 5 from the rear.

Therefore, the injection rod 21 in this embodiment is such that the actuating rod 23 is mounted slidably in the longitudinal direction of the main case 2. If the manipulation button 5 is pushed in further, the pressing face 60 of the engagement pawl 39 will push the actuating rod 23 forward via the locking pawl 24, and the actuating rod 23 will be slid forward on the injection rod 21. That is, the injection rod 21 can absorb the force in the longitudinal direction by the sliding of the actuating rod 23. Therefore, the injection rod 21 itself will not be subjected to a large force, and no damage or other undesirable situations will occur.

Furthermore, since the injection rod 21 does not receive a large force, it can be made thinner and more lightweight while still maintaining adequate strength. This light injection rod 21 can perform a puncture operation with a small injection force, so only a small biasing force to the front side of the main spring 34 is needed. Thus, during a puncture operation, the snapping noise will not be loud when puncture cam 30 pulled by the main spring 34 hits the rib 48. As a result, the user will be less afraid of the puncture, and this also makes the puncture instrument 1 more convenient to use.

As described above, the puncture needle cartridge 4 in this embodiment comprises the lancet main body 6 including the connector 8 to the puncture instrument 1 on the rear end side, the puncture needle cover 9 on the front end side, and the breakaway part 10 in the middle; the puncture needle 11 that is embedded in the lancet main body 6 across the breakaway part 10 of the lancet main body 6; and the lancet case 7 that is mounted to the outer periphery in the middle of the lancet main body 6. The puncture needle cover 9 of the lancet main body 6 includes the guide protrusions 12 that stick out in the outer peripheral direction. The lancet case 7 is provided with the spiral guide components 13 so that the lancet case 7 will receive the turning force with the guide protrusions 12, from its front end toward the rear. The slide protrusions 14, which stick out in the outer peripheral direction, are provided further to the rear than the breakaway part 10 of the lancet main body 6. Also, the slide grooves 15 that guide the sliding of the slide protrusions 14 in the longitudinal direction are provided to the lancet case 7.

With the above configuration, the puncture needle cartridge 4 is easier to use when it is being mounted to the puncture instrument 1. Specifically, the puncture needle cartridge 4 in this embodiment itself has a rotation mechanism for rotating the side of the lancet main body 6 to the rear of the breakaway part 10 within the puncture needle cartridge 4, which breaks the breakaway part 10, along with the mounting operation of the puncture needle cartridge 4 to the puncture instrument 1. Therefore, a user can mount the puncture needle cartridge 4 to the puncture instrument 1 merely by pushing the front end opening 3 of the puncture instrument 1 that is held by the user in one hand, down toward the upright puncture needle cartridge 4, and this also breaks the breakaway part 10 and exposes the puncture needle 11. As a result, the breakaway part 10 can be reliably broken, and the subsequent puncture operation can be carried out properly.

The puncture instrument 1 to which the puncture needle cartridge 4 in this embodiment is mounted includes the locking member 28 rotatably supported by the main rod 19 portion between the injection rod 21 and the manipulation button 5. This locking member 28 has the engagement pawl 39 that engages with the locking pawl 24 of the actuating rod 23, and the push-out tab 40 that comes into contact with the front end side of the manipulation button 5, and is provided with the locking member spring 41 that biases the engagement pawl 39 of the locking member 28 toward the locking pawl 24.

With this configuration, the locking member 28 is rotated by manipulation of the manipulation button 5, and the puncture operation is carried out when the engagement pawl 39 and the locking pawl 24 are disengaged by this rotation, and the injection rod 21 is shot. Then, the locking member 28 is pushed to the front end opening 3 side via the push-out tab 40 by manipulation of the manipulation button 5, and when the pushed locking member 28 pushes the main rod 19 to the front end side via the shaft support, the disposal operation of the puncture needle cartridge 4 is carried out. That is, with the puncture instrument 1 pertaining to this embodiment, the locking member 28 can switch the manipulation of the single manipulation button 5 between two operations, namely, the "puncture operation" of the puncture instrument 1 and the "disposal operation" of the puncture needle cartridge 4. As a result, the puncture instrument 1 is extremely convenient to use, and this facilitates the series of puncture-related operations.

Specifically, first the puncture operation is performed by rotating the locking member 28 through manipulation of the manipulation button 5, and disengaging the engagement pawl 39 and the locking pawl 24 by this rotation so that the injection rod 21 is shot. Next, the disposal operation of the puncture needle cartridge 4 is performed by pushing the locking member 28 to the front end opening side via the push-out tab 40 through manipulation of the manipulation button 5, and pushing the main rod 19 via the shaft support 38 with the pushed locking member 28. Therefore, since the puncture operation and disposal operation can be performed with a single button while the puncture instrument 1 is held in one hand, even a person who is not yet accustomed to handling the puncture instrument 1 will make fewer mistakes.

Furthermore, the puncture needle cartridge 4 in this embodiment has a rotation mechanism for rotating the side of the lancet main body 6 to the rear of the breakaway part 10 in the puncture needle cartridge 4 in one direction and rotating the front side in the other direction, along with the mounting operation of the puncture needle cartridge 4 to the puncture instrument 1, so that the breakaway part 10 is broken by this rotation in two opposite directions.

Accordingly, the user can mount the puncture needle cartridge 4 merely by pushing the front end opening of the puncture instrument 1 that is held by the user in one hand, down toward the upright puncture needle cartridge 4, and this also breaks the breakaway part 10 and exposes the puncture needle 11, and completes the preparation for puncture. As a result, since the mounting operation can be performed while the puncture instrument 1 is held in one hand, even a person who is not yet accustomed to handling the puncture instrument 1 will make fewer mistakes, the device will be extremely easy to use, and the series of puncture-related operations can be facilitated.

As discussed above, when the puncture instrument 1 or the puncture needle cartridge 4 in this embodiment is used, a series of puncture-related operations (mounting operation, puncture operation, and disposal operation) can be performed merely by operating one button while the puncture instrument 1 is held in one hand, so the device is extremely easy to use and the series of puncture-related operations can be facilitated.

Embodiment 2

The puncture needle cartridge 4' pertaining to Embodiment 2 will now be described through reference to FIGS. 22 to 25.

The puncture needle cartridge 4' pertaining to Embodiment 2 differs from Embodiment 1 in the configuration of slide protrusions 14' provided to a lancet main body 6'. The other components that are the same as in Embodiment 1 will be numbered the same and not described again in detail.

The lancet case 7 in Embodiment 1 is provided with the slide receiver 61 that hits the distal ends of the slide protrusions 14 provided to the lancet main body 6 when the lancet main body 6 is slid forward to be discarded as shown in FIGS. 20 and 21. Therefore, when the slide receiver 61 comes into contact with the distal ends of the slide protrusions 14 after the puncture needle cartridge 4 is ejected, the forward sliding of the lancet main body 6 is stopped. Accordingly, the puncture needle 11 will not protrude from the puncture needle cartridge 4, and the puncture needle cartridge 4 can be handled safely.

Figure 22:
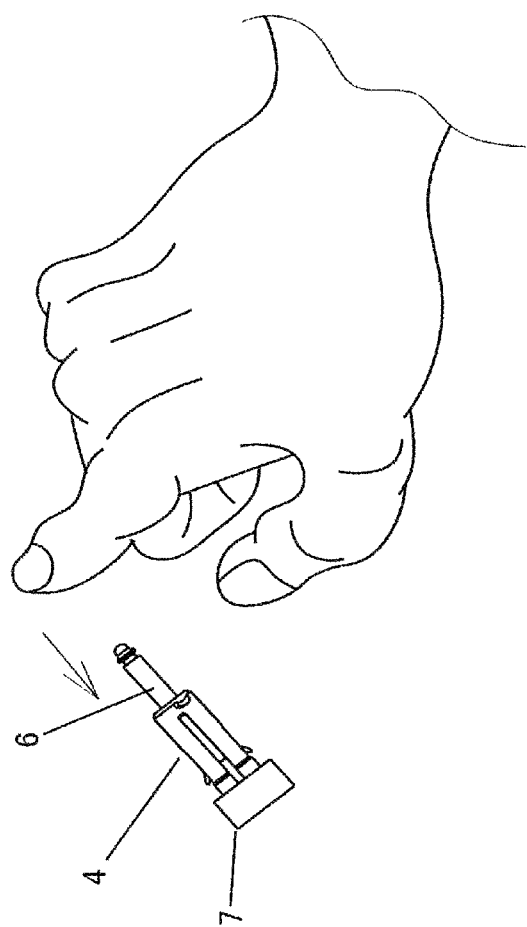
FIG. 22 shows the usage state of this puncture needle cartridge.

However, as indicated by the arrow in FIG. 22, the lancet body 6 is sometimes pushed forward very hard by the user. When this happens, after yielding to the force of the user and spreading outward, the slide protrusions 14 bend rearward, and therefore there is the risk that the lancet body 6 will move forward and the puncture needle 11 will come out of the puncture needle cartridge 4.

Figure 23:
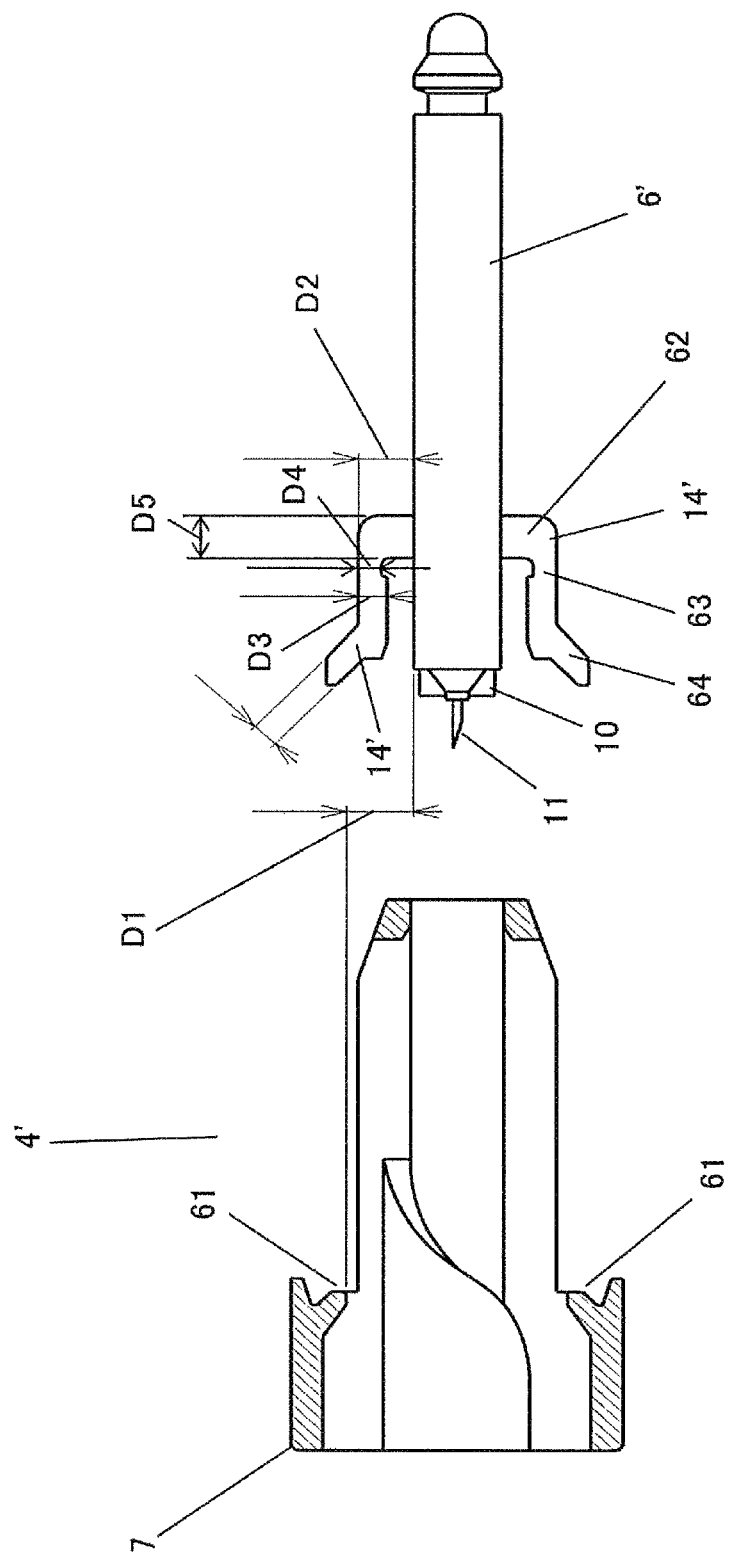
FIG. 23 is an exploded cross section of the puncture needle cartridge pertaining to Embodiment 2.
Figure 24:
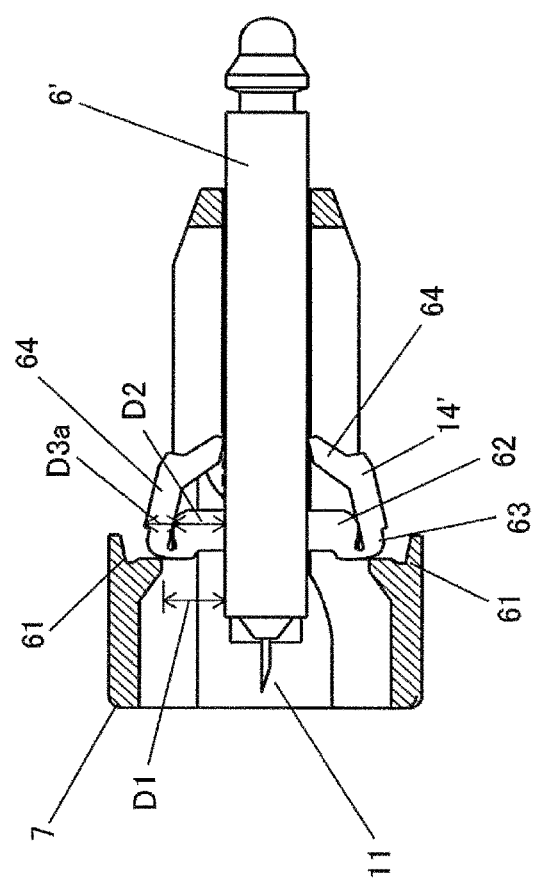
FIG. 24 is a cross section of this puncture instrument.

As shown in FIG. 23, the slide protrusions 14' of the lancet main body 6' in Embodiment 2 have a hook shape extending along the axis of the lancet body 6', and are each provided with a projecting part 62 (an example of a projecting part) that projects outward from the lancet body 6', a linking part 63 (an example of a linking part) that is formed contiguous with the projecting part 62, and a contact part 64 (an example of a contact part) that extends forward (to the breakaway part 10 side) from the linking part 63 and comes into contact with the slide receiver 61 of the lancet case 7. As shown in FIG. 24, the contact part 64 is linked to the linking part 63 rotatably in the axial direction of the lancet main body 6' around the linking part 63. That is, since the linking part 63 is thin and flexible, the contact part 64 is able to rotate along the axial direction of the lancet main body 6'.

As shown in FIG. 24, when the user pushes the lancet main body 6' forward very hard, and the slide protrusions 14' in contact with the slide receiver 61 yield to the user's force, the contact parts 64 spread outward and then bend to the rear, resulting in a state in which they are folded over the projecting parts 62. At this point, with the puncture needle cartridge 4' in this embodiment, the spacing D1 between the outer surface of the lancet main body 6' and the slide receiver 61 of the lancet case 7, the height D2 at which the projecting parts 62 stick out from the lancet main body 6', and the thickness D3a of the contact parts 64 in a direction perpendicular to the axis of the lancet main body 6' have the following relation.

$$D1 < D2 + D3a$$

Therefore, as shown in FIG. 24, even if the user tries as hard as he can to push the lancet main body 6' in further, since the spacing D1 between the outer surface of the lancet main body 6' and the slide receiver 61 of the lancet case 7 is less than the sum of adding the height D2 of the projecting parts 62 to the thickness D3a of the folded-over contact parts 64, the lancet main body 6' will not move forward any further. Therefore, the puncture needle 11 will not come out of the puncture needle cartridge 4'. As a result, the puncture needle cartridge 4' can be handled safely after the disposal operation.

Also, the hook-shaped slide protrusions 14' in this embodiment are formed so that the bending strength of the linking part 63 is lower than that of the projecting part 62 and the contact part 64. More specifically, as shown in FIG. 23, the thickness D4 of the linking part 63 in a direction perpendicular to the major axis of the slide protrusion 14' is less than the thickness D3 of the contact part 64 in a direction perpendicular to the major axis of the slide protrusion 14' and the thickness D5 of the projecting part 62 in a direction of the major axis of the slide protrusion 14'. This reduction in thickness makes the bending strength of the linking parts 63 lower than that of the projecting parts 62 and the contact parts 64. Accordingly, the contact parts 64 of the slide protrusions 14' can be bent outward and rearward at the linking parts 63, which are the weakest parts, so the contact parts 64 can be folded over the projecting parts 62 as shown in FIG. 24. Therefore, the puncture needle 11 will not come out of the puncture needle cartridge 4'.

As shown in FIG. 23, the slide protrusions 14' in this embodiment are bent substantially parallel to the lancet main body 6' from the linking parts 63 toward the breakaway part 10 side, and are spread outside of the lancet main body 6' from the middle forward to form the contact parts 64. Accordingly, as shown in FIG. 24, when the contact parts 64 is folded over the projecting parts 62, the distal ends of the portion of the contact parts 64 that spreads outside of the lancet main body 6' from the middle part forward hit the lancet main body 6' and form a bridge. Therefore, the contact parts 64 can be properly folded over the projecting parts 62, and the puncture needle 11 will not come out of the puncture needle cartridge 4'.

Figures 25A, 25B:
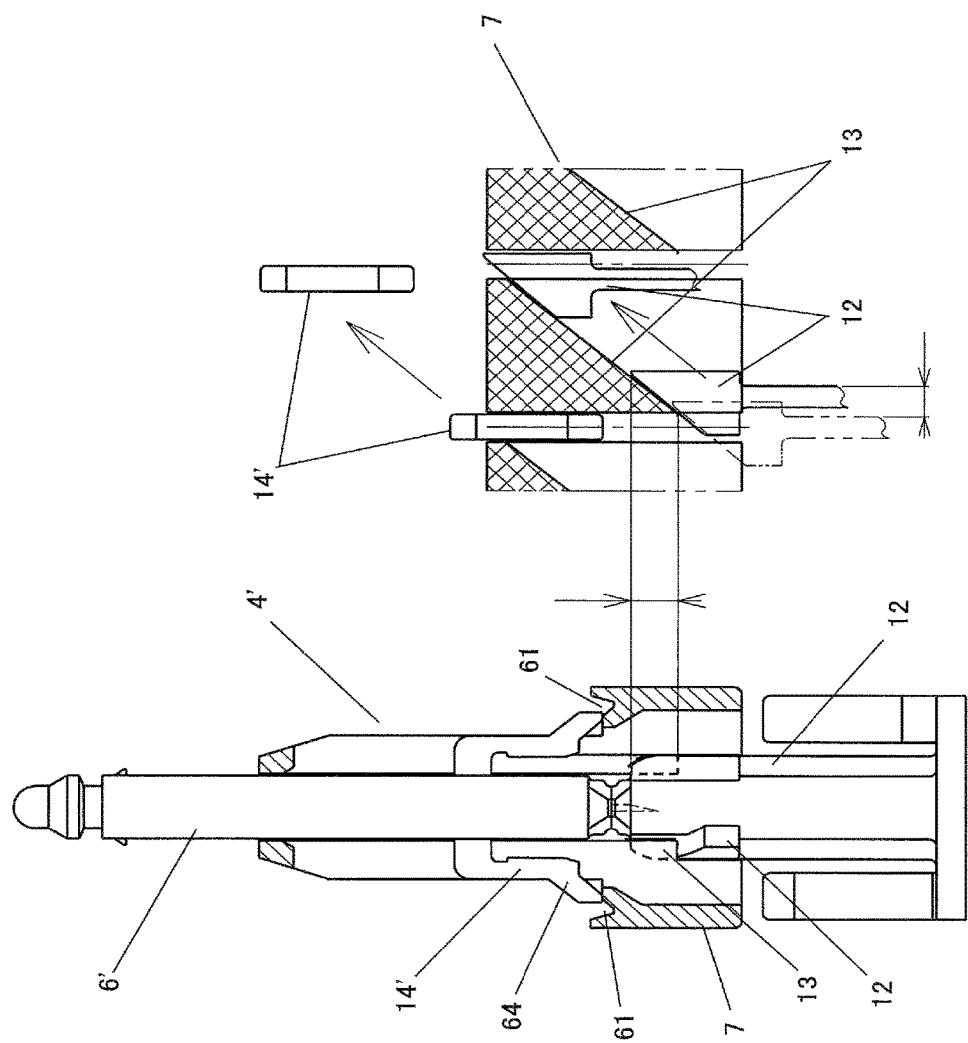
FIG. 25A is a cross section of this puncture needle cartridge.
FIG. 25B is a development view of the main components of this puncture needle cartridge.

Also, in this embodiment, in a state in which the contact parts 64 of the slide protrusions 14' provided to the lancet main body 6' are in contact with the slide receiver 61 of the lancet case 7 as shown in FIG. 25A, the guide protrusions 12 of the lancet main body 6' are in contact with the spiral guide components 13 of the lancet case 7 as shown in FIG. 25B. Consequently, the spiral guide components 13 reliably slide over the guide protrusions 12.

More specifically, the puncture needle cartridge 4' is manufactured through the following steps. First, the lancet case 7 is placed over the outer peripheral part of the lancet main body 6' and pushed down, and the spiral guide components 13 of the lancet case 7 hit the guide protrusions 12 of the lancet main body 6'. From this state, the lancet case 7 is pushed down while rotating, which starts to twist the breakaway part 10. After this, at the point where the lancet case 7 has been rotated 30 degrees, for example, as shown in FIG. 25A, the slide receiver 61 of the lancet case 7 drops down to the lower side of the slide protrusions 14' of the lancet main body 6', and the lancet case 7 is released at this position. The restorative force produced by the twisting of the breakaway part 10 then tries to rotate and push the lancet case 7 back up the other way, but the contact parts 64 of the slide protrusions 14' are in contact with the slide receiver 61, and this stops the lancet case 7. Accordingly, the elasticity of the slide protrusions 14' keeps the lancet case 7 stationary at the position where the spiral guide components 13 have suitably ridden up onto the guide protrusions 12. As a result, when the user handles the puncture needle cartridge 4', the guide components 13 will not separate from the guide protrusions 12, so in the subsequent mounting operation, the spiral guide components 13 can be properly slid over the guide protrusions 12.

As discussed above, the puncture needle cartridge 4' pertaining to Embodiment 2 is a modification of the puncture needle cartridge 4 in Embodiment 1, and further facilitates handling, especially during the disposal operation.

Embodiment 3

Figure 28:
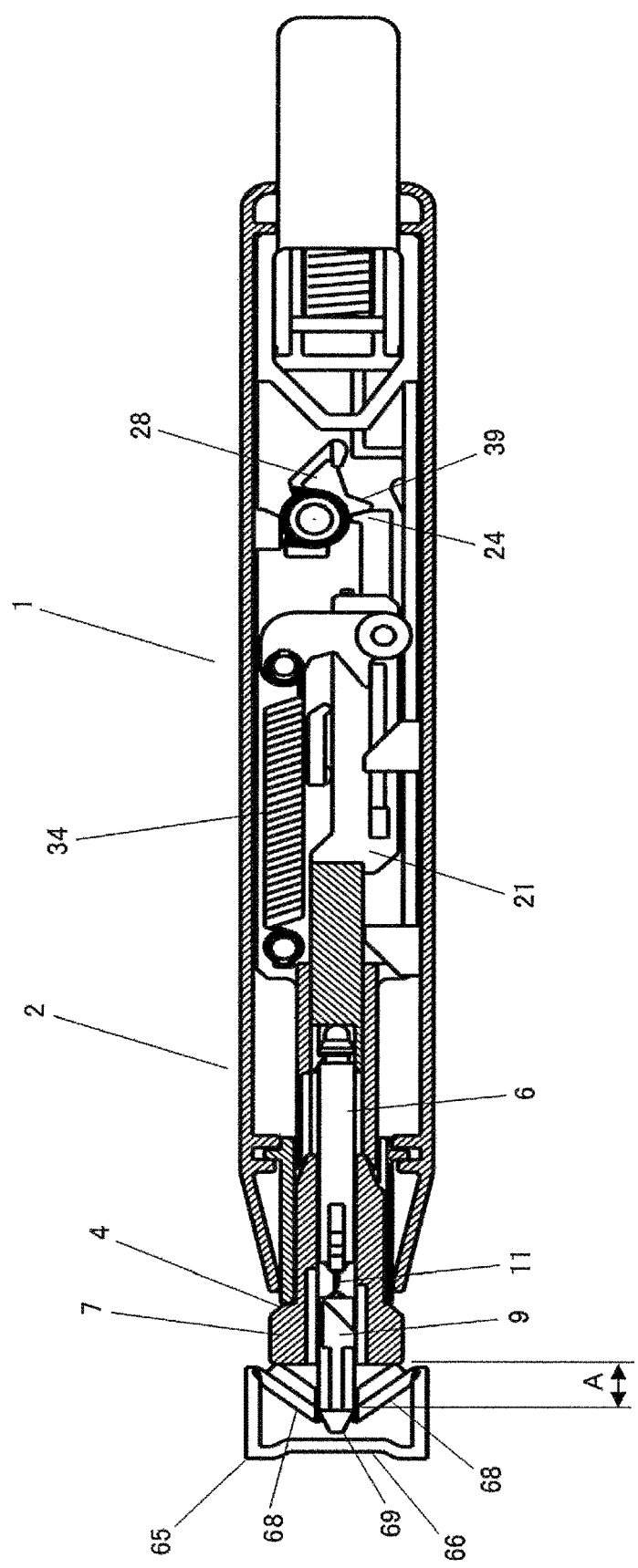
FIG. 28 is a cross section of this puncture instrument.

The puncture needle cartridge 4" pertaining to Embodiment 3 will now be described through reference to FIGS. 26 to 28.

3-1 Configuration

FIG. 26 shows the puncture needle cartridge 4" in Embodiment 3. This puncture needle cartridge 4" differs from the puncture needle cartridge 4 pertaining to Embodiment 1 and shown in FIG. 2 in that a separation member 65 that is substantially cuboid in shape is provided as substitute for the base component 16 in Embodiment 1. The other components that are the same as in Embodiment 1 will be numbered the same and not described again in detail.

Figure 26A:
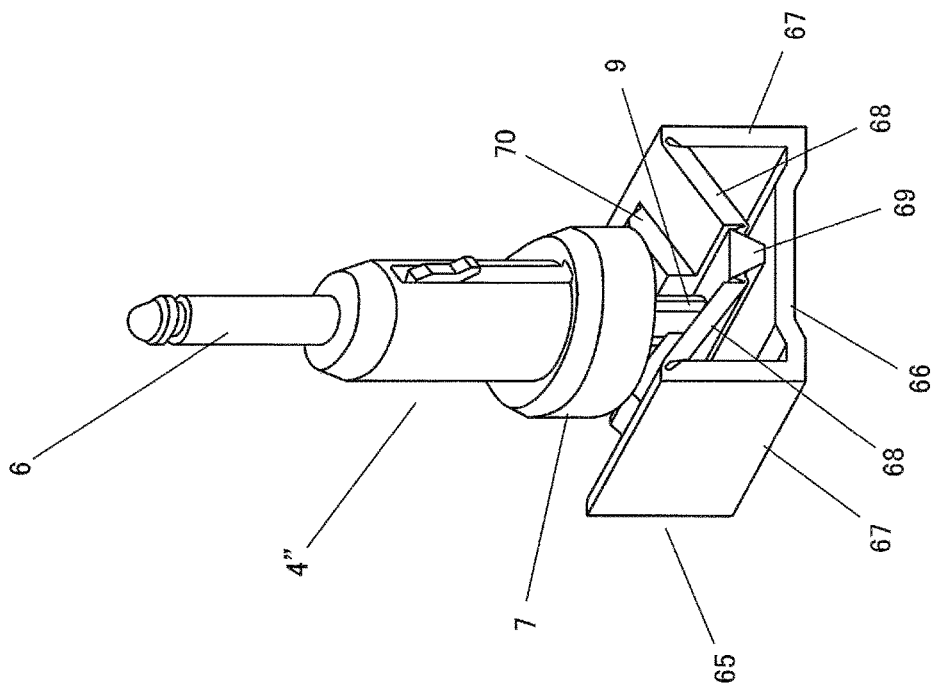
FIG. 26A is an oblique view of one state of the puncture needle cartridge pertaining to Embodiment 3.
Figure 26B:
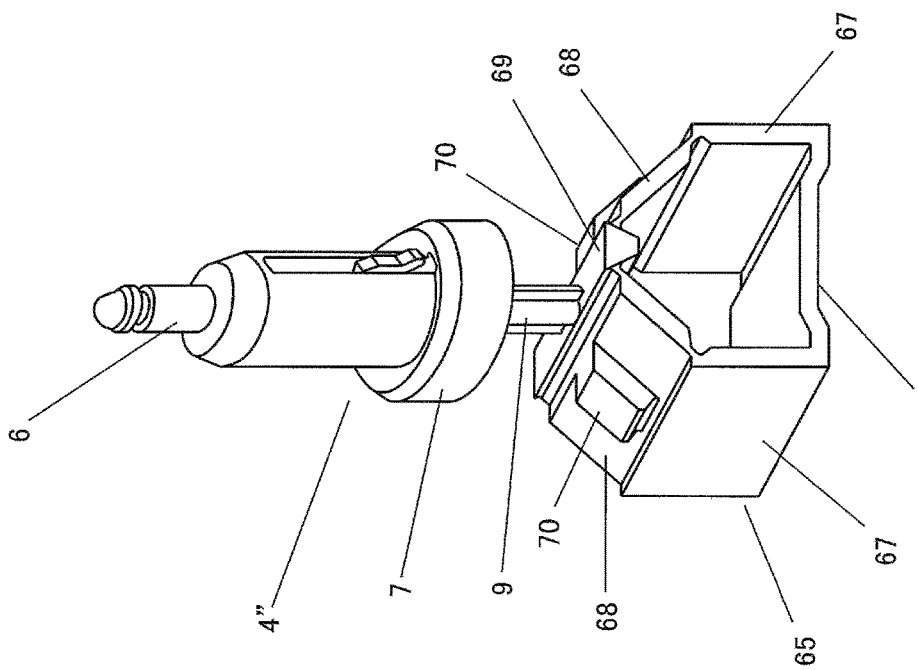
FIG. 26B is an oblique view of another state of this puncture needle cartridge.

The separation member 65 is configured to achieve a deformation operation from a state in which the middle part of the top face connected to the puncture needle cover 9 protrudes upward toward the puncture needle cover 9 side as shown in FIG. 26A, to a state in which the middle part protrudes downward, that is, to the opposite side from the puncture needle cover 9 side, as shown in FIG. 26B. The deformation of the separation member 65, that is, the operation in which the middle part of the top face of the separation member 65 is deformed from upward to downward, allows the puncture needle cover 9 connected to the middle part of the top face to be pulled away from the puncture needle 11.

More specifically, with the puncture needle cartridge 4″ in this embodiment, the front end of the lancet main body 6 is provided with the separation member 65, which separates the side of the lancet main body 6 that is ahead of the breakaway part 10 (the lower side in FIG. 26) from the side of the lancet main body 6 that is behind the breakaway part 10 (the upper side in FIG. 26). This separation member 65 is substantially box-shaped, with the bottom face disposed to face in a direction perpendicular to the axis of the lancet main body 6 on the front end side of the cylindrical lancet main body 6 (the lower side in FIG. 26). The separation member 65 comprises a base face part 66, side face parts 67, movable face parts 68, and an attachment component 69. The base face part 66 is in the form of a thin rectangular plate, and constitutes the bottom face, which is disposed to be perpendicular to the axis of the lancet main body 6. The side face parts 67 are in the form of a thin rectangular plate, and are formed extending vertically to the lancet main body 6 side (the upper side in FIG. 26), from the left and right sides of the base face part 66. The movable face parts 68 are in the form of a thin rectangular plate, and are each formed so as to be bent movably toward the inside beyond the rear end side (the upper side in FIG. 26) of the left and right side face parts 67, that is, toward the other movable face part 68. The attachment component 69 is in the form of a long rod, is disposed opposite the base face part 66 on the inside of the left and right movable face parts 68, and is attached movably with respect to the left and right movable face parts 68. That is, the left and right movable face parts 68 form the top face of the separation member 65, and the attachment component 69 is attached to the middle part of this top face.

The inside of the left and right movable face parts 68 is sloped to the lancet main body 6 side, and this causes the attachment component 69 in the middle of the top face of the separation member 65 to stick out to the lancet main body 6 side. This protruding attachment component 69 is connected to the puncture needle cover 9 of the lancet main body 6. The base face part 66, side face parts 67, movable face parts 68, and attachment component 69 that constitute the separation member 65 are integrally molded from a synthetic resin along with the lancet main body 6, and the separation member 65 and the lancet main body 6 are integrated.

Also, the side face parts 67 (in the form of thin plates) molded integrally with the separation member 65 are configured so that their elasticity can be utilized to elastically deform the rear end side (that is, the top face side of the separation member 65) toward the outside. Accordingly, the middle part of the top face of the separation member 65 can be elastically deformed from upward to downward. This deformation operation will be described in detail below.

Thin-walled portions are provided between the side face parts 67 and the movable face parts 68, and between the movable face parts 68 and the attachment component 69. Accordingly, bending (movement) between the side face parts 67 and the movable face parts 68, and between the movable face parts 68 and the attachment component 69 can be carried out smoothly at these thin-walled portions, so the separation member 65 can be easily deformed.

3-2 Operation

The mounting operation for the puncture needle cartridge 4″ configured as above will now be described through reference to FIG. 27. FIGS. 27A to 27F are side views of the main components of the puncture needle cartridge 4″ and the puncture instrument 1. The puncture instrument 1 and the lancet case 7 are shown in cross section to facilitate understanding.

As shown in FIG. 27A, when the rear side (the upper side in FIG. 27A) of the puncture needle cartridge 4″ is inserted through the front end opening 3 of the puncture instrument 1, the distal end of the main case 2 of the puncture instrument 1 pushes on the lancet case 7, and the lancet case 7 slides toward the separation member 65. This sliding starts twisting the breakaway part 10 as mentioned above.

Then, as shown in FIG. 27B, when the front end side (the lower side in FIG. 27B) of the lancet case 7 slides to the position of the attachment component 69 that protrudes on the upper side of the separation member 65, the breakaway part 10 is twisted off.

As shown in FIG. 27C, when the main case 2 is pushed down further, the front end side of the lancet case 7 hits convex components 70 provided to the top faces of the movable face parts 68 of the separation member 65. These convex components 70 protrude to the lancet case 7 side, and the lancet case 7 in contact with the convex components 70 pushes the left and right movable face parts 68 downward via the convex components 70. The left and right movable face parts 68 move so as to reduce the slope on their inside, and push apart the side face parts 67 on both sides.

Then, as shown in FIG. 27D, when there is no more slope to the left and right movable face parts 68 (when they are level), the puncture needle cover 9 sticks out from the front end of the lancet case 7 by substantially the same amount as the amount by which the convex components 70 stick out. Accordingly, the puncture needle 11 that have been covered by the puncture needle cover 9 is exposed by substantially the same amount as the amount by which the convex components 70 stick out.

When the main case 2 is pushed down further, the insides of the left and right movable face parts 68 begin sloping to the base face part 66 side (the lower side in FIG. 27). At this point, the elastic restorative force of the side face parts 67 that have been pushed apart outward causes them to suddenly return to their original shape. Therefore, as shown in FIG. 27E, the insides of the movable face parts 68 are pulled down toward the base face part 66, and this causes the attachment component 69 also to be suddenly pulled down toward the base face part 66. This causes the puncture needle cover 9 to be completely removed from the breakaway part 10. That is, the puncture needle cover 9 is removed from the puncture needle 11, and as a result the puncture needle 11 can be exposed at the front end portion of the lancet main body 6. Since the puncture operation is not yet performed at this point, the puncture needle 11 is still inside the lancet case 7. This concludes the deformation of the separation member 65, and thereafter the separation member 65 maintains its deformed state.

The operation by which the insides of the movable face parts 68 are pulled down toward the base face part 66 happens very suddenly under the elastic restorative force of the side face parts 67, so the movement is sensed as a so-called click. Therefore, this click tells the user in a clear way that the mounting operation of the puncture needle cartridge 4" is finished.

After this, when the user lifts up the main case 2, as shown in FIG. 27F, the deformed separation member 65 separates from the puncture needle cartridge 4". This concludes the mounting operation of the puncture needle cartridge 4".

With the above configuration, the user can carry out the mounting operation of the puncture needle cartridge 4" easily, merely by holding the main case 2, pushing it down toward the puncture needle cartridge 4", and then lifting it up again, and, the user can carry out the subsequent puncture operation favorably.

Furthermore, the puncture operation is performed and the puncture needle cartridge 4" is disposed of in the disposal operation after the puncture needle cartridge 4" has been mounted to the puncture instrument 1 in the mounting operation discussed above. A separation member 65 that has already been separated is sometimes remounted to the puncture needle cartridge 4" and left there until disposal. In view of this, the puncture needle cartridge 4" in this embodiment is designed so that the separation member 65 is deformed after one use as discussed above. Therefore, the used puncture needle cartridge 4" shown in FIG. 26B can be easily distinguished from the unused puncture needle cartridge 4" shown in FIG. 26A. Thus, the user can identify and use an unused puncture needle cartridge 4" for the next measurement.

Furthermore, in this embodiment, even if the user accidentally tries to use a puncture needle cartridge 4" that has already been used once, this reuse can be prevented. Specifically, as discussed above, the puncture needle cartridge 4" in this embodiment is designed so that the separation member 65 is deformed after being used once. Therefore, as shown in FIG. 28, even if the user accidentally inserts a used puncture needle cartridge 4" into the main case 2, the separation member 65 has been deformed and the attachment component 69 is pulled down toward the base face part 66, and the puncture needle cover 9 connected to the attachment component 69 is pulled out by a reuse prevention amount A from the front end of the lancet case 7 toward the base face part 66. That is, the depression amount is lacking by the reuse prevention amount A with respect to the amount of depression that is needed (that is, the amount of depression to the rear of the injection rod 21 by the lancet main body 6 when an unused puncture needle cartridge 4 is used). Because the amount of depression is lacking, the movement distance to the rear of the locking pawl 24 behind the injection rod 21 will be inadequate inside the main case 2, and the locking pawl 24 will not engage with the engagement pawl 39 of the locking member 28. Therefore, the main spring 34 will not store any puncture force, and the puncture operation will not be performed. As a result, improper reuse of a used puncture needle cartridge 4 can be prevented.

In this embodiment, the magnitude of the reuse prevention amount A is greater than the length at which the puncture needle 11 is exposed from the lancet main body 6. Therefore, even if a used puncture needle cartridge 4 is accidentally inserted into the main case 2, and the puncture needle cover 9 is not covering the puncture needle 11 as shown in FIG. 28, since the reuse prevention amount A is set to be greater than the exposure length of the puncture needle 11, the movement distance of the locking pawl 24 behind the injection rod 21 will be inadequate within the main case 2, and the locking pawl 24 will not engage with the engagement pawl 39 of the locking member 28.

Other Embodiments

Embodiments 1 to 3 are described above as examples of the technology disclosed herein, but the technology disclosed herein is not limited to or by these, and can also be applied to embodiments with modifications, substitutions, additions, omissions, and so forth made as needed. Also, the various constituent elements described in the Embodiments 1 to 3 above can be combined to create new embodiments.

The constituent elements illustrated in the appended drawings and discussed in the detailed description can encompass not only those constituent elements that are essential to solving the problem, but also constituent elements that are not essential to solving the problem. Accordingly, just because these non-essential constituent elements are illustrated in the appended drawings and discussed in the detailed description, it should not be concluded that these non-essential constituent elements are essential.

INDUSTRIAL APPLICABILITY

This disclosure can be utilized as a puncture needle cartridge for inserting a needle into a body and withdrawing blood in order to measure biological information, such as a blood glucose level, as well as a puncture instrument to which this cartridge is mounted, and a method for mounting this puncture needle cartridge to a puncture instrument.

The invention claimed is:

1. A puncture instrument having a first end side, which is the side on which a puncture needle cartridge is mounted, and a second end side opposite the first end side, said puncture instrument comprising:
   an elongated main case including an opening on the first end side and on the second end side;
   a main rod provided in the main case;
   an injector rod mounted to the main rod and including a lancet holder on the first end side;
   an actuating rod mounted to the injector rod and including an engagement component on the second end side;
   a first biasing member configured to bias the injector rod toward the first end side;
   a manipulation component provided slidably in and out of the opening on the second end side of the main case; and
   a locking member rotatably supported by a portion of the main rod between the injector rod and the manipulation component, the locking member including a first engaged part configured to engage the engagement component of the actuating rod, a second engaged part configured to abut a portion of the manipulation component on the first end side, and a second biasing member configured to bias the first engaged part toward the engagement component,
   wherein the manipulation component has on the first end side thereof a flat part configured to abut the second engaged part of the locking member, and an inclined part adjacent to the flat part, the inclined part extending to the second end side and being inclined to an axis of the main case, the locking member rotates by an action of mounting the puncture needle cartridge so that the second engaged part rotates from a position opposite the flat part of the manipulation component to a position opposite the inclined part; and the locking member abuts the flat part when the manipulation component is pushed by an action of disposing the puncture needle cartridge so that the locking member slides toward the first end side with the main rod and the puncture needle cartridge is disposed.

2. The puncture instrument according to claim 1, wherein the main rod includes a first stopper configured to stop the second engaged part of the locking member at a position opposite the flat part of the manipulation component when the locking member rotates in a biasing direction of the second biasing member.

3. The puncture instrument according to claim 1, wherein the actuating rod includes an anti-rotation component configured to prevent the first engaged part of the locking member from rotating in a biasing direction of the second biasing member after the first engaged part has been rotated by the engagement component in an opposite direction from the biasing direction.

4. The puncture instrument according to claim 1, wherein the second engaged part of the locking member is in a position opposite the inclined part of the manipulation component when the engagement component of the actuating rod is engaged with the first engaged part of the locking member.

5. The puncture instrument according to claim 1, wherein the main case includes a second stopper configured to stop a rotation of the second engaged part of the locking member in an opposite direction from a biasing direction of the second biasing member when the second engaged part has been rotated in the opposite direction by the inclined part of the manipulation component.

6. The puncture instrument according to claim 1, wherein the main case has an elongated tube shape, and the manipulation component is configured to slide along the axis of the main case.

7. The puncture instrument according to claim 1, wherein the locking member is axially supported at a portion of the main rod, at a position opposite the flat part and the inclined part of the manipulation component.

8. The puncture instrument according to claim 1, wherein the main rod includes a holder insertion tube configured to accommodate the lancet holder of the injector rod, on the first end side, and the holder insertion tube includes a push-out face configured to push out a lancet, on the first end side.

9. The puncture instrument according to claim 1, wherein the first engaged part of the locking member includes a pressing face configured to push the engagement component of the actuating rod toward the first end side.

10. The puncture instrument according to claim 1, further comprising a third biasing member, wherein the actuating rod is mounted slidably in a longitudinal direction along the injector rod, and is biased by the third biasing member toward the second end side.

11. The puncture instrument according to claim 1, wherein the locking member executes a puncture operation of the puncture instrument when the second engaged part rotates from a position opposite the inclined part of the manipulation component in an opposite direction from a biasing direction of the second biasing member.

12. The puncture instrument according to claim 1, wherein when an operation is executed to discard the puncture needle cartridge, the second engaged part comes into contact with the flat part of the manipulation component in a state in which the locking member is restricted in rotation in a biasing direction of the second biasing member.

13. A method for using the puncture instrument according to claim 1, comprising:

mounting the puncture needle cartridge to the puncture instrument by inserting a lancet of the puncture needle cartridge into the opening on the first end side of the main case and mounting the lancet to the lancet holder of the injector rod of the puncture instrument;

injecting the puncture needle from a front end of the puncture needle cartridge by moving the manipulation component toward the first end side of the main case; and then, discarding the puncture needle cartridge from the opening on the first end side of the main case by moving the manipulation component toward the first end side of the main case after the puncture operation to remove the lancet from the lancet holder.

14. A puncture instrument having a first end side, which is the side on which a puncture needle cartridge is mounted, and a second end side opposite the first end side, said puncture instrument comprising:

an elongated main case including an opening on the first end side and on the second end side;

a main rod provided in the main case;

an injector rod mounted to the main rod and including a lancet holder on the first end side;

an actuating rod mounted to the injector rod and including an engagement component on the second end side;

a first biasing member configured to bias the injector rod toward the first end side;

a manipulation component provided slidably in and out of the opening on the second end side of the main case; and a locking member rotatably supported by a portion of the main rod between the injector rod and the manipulation component, the locking member including a first engaged part configured to engage the engagement component of the actuating rod, a second engaged part configured to abut a portion of the manipulation component on the first end side, and a second biasing member configured to bias the first engaged part toward the engagement component, wherein the manipulation component has on the first end side thereof a flat part configured to abut the second engaged part of the locking member, and two inclined parts adjacent to the flat part, the inclined parts extending from an axial area of flat part and towards the second end side of the main case, the inclined parts further extending away from each other and towards opposite exterior sides of the main case, and the locking member rotates by an action of mounting the puncture needle cartridge so that the second engaged part moves from a position opposite the flat part of the manipulation component to a position opposite to one of the two inclined parts.

* * * * *